US006086900A

United States Patent [19]
Draper

[11] Patent Number: 6,086,900
[45] Date of Patent: Jul. 11, 2000

[54] METHODS AND COMPOSITIONS FOR USING MEMBRANE-PENETRATING PROTEINS TO CARRY MATERIALS ACROSS CELL MEMBRANES

[75] Inventor: Rockford Draper, Plano, Tex.

[73] Assignee: Board of Regents, The University of Texas Systems, Austin, Tex.

[21] Appl. No.: 09/047,148

[22] Filed: Mar. 24, 1998

Related U.S. Application Data

[60] Provisional application No. 60/042,056, Mar. 26, 1997.
[51] Int. Cl.[7] .............................. A61K 39/44; C12N 5/10; C07K 17/02
[52] U.S. Cl. ............................. 424/282.1; 514/2; 514/44; 435/455; 435/320.1; 435/358; 435/357; 435/367; 435/372.2; 435/372.3; 530/350; 530/387.1; 536/23.1; 536/23.4; 536/23.5; 536/23.7
[58] Field of Search ................................ 435/320.1, 69.1, 435/455, 358, 357, 367, 372.2, 372.3; 530/350, 387.1; 424/282.1; 514/2, 44; 536/23.1, 23.4, 23.5, 23.7

[56] References Cited

FOREIGN PATENT DOCUMENTS

| WO 91/09871 | 7/1991 | WIPO . |
| WO 94/04696 | 3/1994 | WIPO . |
| WO 94/13316 | 6/1994 | WIPO . |

OTHER PUBLICATIONS

Bau and Draper, "Ricin intoxicates End4 mutants that have an aberrant Golgi complex," *J. Biol. Chem.*, 268:19939–19942, 1993.

Benhar et al., "Pseudomonas exotoxin A mutants: replacement of surface–exposed residues in domain III with cysteine residues that can be modified with polyethyleme glycol in a site–specific manner," *J. Biol. Chem.*, 269(18):13398–13404, 1994.

Bosshart et al., "The cytoplasmic domain mediates localization of furin to the trans–Golgi network en route to the endosomal/lysosomal system," *J. Cell Biol.*, 126, 1157–1172, 1994.

Braakman et al., "Role of ATP and disulphide bonds during protein folding in the endoplasmic reticulum," *Nature* 356:260–262, 1992.

Burbage et al., "Ricin fusion toxin targeted to the human granulocyte–macrophage colony stimulating factor receptor is selectively toxic to acute myeloid leukemia cells," *Leuk Res*, 21(7):681–690, 1997.

Chaudhary et al., "Pseudomonas exotoxin contains a specific sequence at the carboxyl terminus that is required for cytotoxicity," *Proc. Natl. Acad. Sci. USA*, 87:308–312, 1990.

Chaudhary et al., "A recombinant immunotoxin consisting of two antibody variable domains fused to Pseudomonas exotoxin," *Nature*, 339(6223):394–397, 1989.

Chaudry et al., "A dipeptide insertion in domain I of exotoxin A that impairs receptor binding," *J. Biol. Chem.*, 264(25):15151–15156, 1989.

Chiron et al., "Cleavage of Pseudomonas exotoxin and diphtheria toxin by a furin–like enzyme prepared from beef liver," *J. Biol. Chem.*, 269:18167–18176, 1994.

Cosson and Letourneur, "Coatomer interaction with di–lysine endoplasmic reticulum retention motifs," *Science*, 263:1629–1631, 1994.

Demidov et al., "Stability of peptide nucleic acids in human serum and cellular extracts," *Biochem. Pharmacol.*, 48:1310–1313, 1994.

Derossi et al., "Trojan peptides: the penetratin system for intracellular delivery," *Cell Biol.*, 8:84–87, 1998.

Douglas and Collier, "Exotoxin A of *Pseudomonas aeruginosa*: substitution of glutamic acid 553 with aspartic acid drastically reduces toxicity and enzymatic activity," *J. Bacteriol.*, 169(11):4967–4971, 1987.

Douglas et al., "Exotoxin A of *Pseudomonas aeruginosa*: active, cloned toxin is secreted into the periplasmic space of *Escherichia coli,*" *J. Bacteriol.*, 169(11):4962–4966, 1987.

Endo et al., "The mechanism of action of ricin–And related toxic lectins on eukaryotic ribosomes: the site and the characteristics of the modification in 28 S ribosomal RNA caused by the toxins,"*J. Biol. Chem.*. 262:5908–5912, 1987.

Frankel and Pabo, "Cellular uptake of the tat protein from human immunodeficiency virus," *Cell*, 55(6):1189–1193, 1988.

Gordon and Leppla, "Proteolytic activation of bacterial toxins: role of bacterial and host cell proteases," *Infect. Immun.*, 62:333–340, 1994.

Gray et al., "Cloning, nucleotide sequence, and expression in *Escherichia coli* of the exotoxin A structural gene of *Pseudomonas aeruginosa,*" *Proc. Natl. Acad. Sci. USA*, 81:2645–2649, 1984.

Hanvey et al., "Antisense properties of peptide nucleic acids," *Science*, 258:1481–1485, 1992.

Hobbie et al., "Isolation of three classes of conditional lethal Chinese hamster ovary cell mutants with temperature–dependent defects in low density lipoprotein receptor stability and intracellular membrane transport," *J. Biol. Chem.*, 269:20958–20970, 1994.

Hudson and Grillo, "Brefeldin A enhancement of ricin–A–chain immunotoxins and blockade of intact ricin, modeccin and abrin," *J. Biol. Chem.*, 266:18586–18592, 1991.

Iglewski and Sadoff, "Toxin inhibitors of protein synthesis: production, purification, and assay of *Pseudomonas aeruginosa* toxin A," *Methods Enzymol.*, 60:780–793, 1979.

Inocencio et al., "Furin activates Pseudomonas exotoxin A by specific cleavage in vivo and in vitro," *J. Biol. Chem.*, 269:31831–31835, 1994.

(List continued on next page.)

*Primary Examiner*—David Guzo
*Attorney, Agent, or Firm*—Arnold, White & Durkee

[57] ABSTRACT

The present invention provides methods and compositions delivery of agents into the cytoplasm of cells. Particularly, it concerns the use of membrane-penetrating toxin proteins to deliver drugs to the cytoplasm of target cells.

62 Claims, 6 Drawing Sheets

OTHER PUBLICATIONS

Kao and Draper, "Retention of secretory proteins in an intermediate compartment and disappearance of the Golgi complex in an End4 mutant of Chinese hamster ovary cells," *J. Cell Biol.*, 117:701–715, 1992.

Kitamoto et al., "Enterokinase, the initiator of intestinal digestion, is a mosaic protease composed of a distinctive assortment of domains," *Proc. Natl. Acad. Sci. USA*, 91:7588–7592, 1984.

Kounnas et al,. "The 2–macroglobulin receptor/low density lipoprotein receptor–related protein binds and internalizes Pseudomonas exotoxin A," *J. Biol. Chem.*, 267:12420–12423, 1992.

Leduc et al., "Activation of human furin precursor processing endoprotease occurs by an intramolecular autoproteolyic cleavage," *J. Biol. Chem.*, 267:14304–14308, 1992.

Lemaitre et al., "Specific antiviral activity of a poly(L–lysine)–conjugated oligodeoxyribonucleotide sequence complementary to vesicular stomatitis virus N protein mRNA initiation site," *Proc. Natl. Acad. Sci. USA*, 84:648–652, 1987.

Leonetti et al., "Antibody–targeted liposomes containing oligodeoxyribonucleotides complementary to viral RNA selectively inhibit viral replication," *Proc. Natl. Acad. Sci. USA*, 87:2448–2451, 1990.

Leppla, "Large–scale purification and characterization of the exotoxin of *Pseudomonas aeruginosa*," *Infect. Immun.*, 14(4):1077–1086, 1976.

Letourneur et al., "Coatomer is essential for retrieval of dilysine–tagged proteins to the endoplasmic reticulum," *Cell*, 79:1199–1207, 1994.

Lidor et al., "In vitro expression of the diphtheria toxin A–chain gene under the control of human chorionic gonadotropin gene promoters as a means of directing toxicity to ovarian cancer cell lines," *Am. J. Obstet. Gynecol.*, 177(3):579–585, 1997.

Lukac and Collier, "Restoration of enzymic activity and cytotoxicity of mutant, E553C, *pseudomonas aeruginosa* exotoxin A by reaction with iodoacetic acid," *J. Biol. Chem.* 263:6146–6149, 1988.

Lukac and Collier, "*Pseudomonas aeruginosa* exotoxin A: effects of mutating tyrosine–470 and tyrosine–481 to phenylalanine," *Biochem.*, 27:7629–7632, 1988.

Lukac et al., "Toxoid of *Pseudomonas aeruginosa* exotoxin A generated by deletion of an active–site residue," *Infect. Immun.*, 53:3095–3098, 1988.

Madshus and Collier, "Effects of eliminating a disulfide bridge within domain II of *Pseudomonas aeruginosa* exotoxin A," *Infect. Immun.*, 57:1873–1878, 1989.

Massuda et al., "Regulated expression of the diphtheria toxin A chain by a tumor–specific chimeric transcription factor results in selective toxicity for *alveolar rhabdomyosarcoma* cells," *Proc. Natl. Acad. Sci. USA*, 94(26):14701–14706, 1997.

Miesenack and Rothman, "The capacity to retrieve escaped ER proteins extends to the trans–most cisterna of the Golgi stack," *J. Cell Biol.*, 129:309–319, 1995.

Moehring et al., "Expression of mouse furin in a Chinese hamster cell resistant to Pseudomonas exotoxin A and viruses complements the genetic lesion," *J. Biol. Chem.*, 268:2590–2594, 1993.

Nakano et al., "A temperature–sensitive Chinese hamster ovary cell mutant pleiotropically defective in protein export," *Biochim. Biophys. Acta*, 845:324–332, 1985.

Odin and Obrink, "Quantitative determination of the organ distribution of the cell adhesion molecule cell–CAM 105 by radioimmunoassay," *Exp. Cell Res.*, 171:1–15, 1987.

Ogata et al., "Processing of Pseudomonas exotoxin by a cellular protease results in the generation of a 37,000–Da toxin fragment that is translocated to the cytosol," *J. Biol. Chem.*, 265:20678–20685, 1990.

Ogata et al., "Cell–mediated cleavage of Pseudomonas exotoxin between $Arg^{279}$ and $Gly^{280}$ generates the enzymatically active fragment which translocates to the cytosol," *J. Biol. Chem.*, 267:25396–25401, 1992.

Olsnes and Pihl, "Toxin lectins and related proteins," In: *Molecular Action of Toxins and Viruses*, P. Cohen, and S. van Heyningen, eds. (Amsterdam: Elsevier/North Holland), pp. 51–105, 1982.

Olsnes and Sandvig, "Entry of polypeptide toxins into animal cells," In: *Endocytosis*, I. Pastan and M. C. Willingham, eds., Penum Publishing Corporation, New York, pp. 195–234, 1985.

Pastan and FitzGerald, "Recombinant toxins for cancer treatment," *Science*, 254:1173–1177, 1991.

Pastan et al., "Recombinant toxins as novel therapeutic agents," *Ann. Rev. Biochem.*, 61:331–354, 1992.

Pelham et al., "Toxin entry: how reversible is the secretory pathway?," *Trends Cell Biol.*, 2:183–185, 1992.

Prior et al., "Barnase toxin: a new chimeric toxin composed of Pseudomonas exotoxin A and barnase," *Cell*, 64:1017–1023, 1991.

Prior et al., "Translocation mediated by domain II of Pseudomonas exotoxin A: transport of barnase into the cytosol," *Biochem.*, 31(14):3555–3559, 1992.

Sandvig et al., "Retrograde transport of endocytosed Shiga toxin to the endoplasmic reticulum," *Nature*, 358:510–512, 1992.

Sandvig et al., "Retrograde transport from the Golgi complex to the ER of both shiga toxin and the nontoxic shiga B–fragment is regulated by butyric acid and cAMP," *J. Cell Biol.*, 126:53–64, 1994.

Scatchard, "The attraction of proteins for small molecules and ions," *Ann. N.Y. Acad. Sci.*, 51:660–672, 1949.

Serrano et al., "A new regulatory motif in cell–cycle control causing specific inhibition of cyclin D/CDK4," *Nature*, 366:704–707, 1993.

Serrano et al., "Inhibition of Ras–induced proliferation and cellular transformation by $p16^{INK4}$," *Science*, 267:249–252, 1995.

Siegall et al., "Functional analysis of domains II, Ib and III of Pseudomonas exotoxin," *J. Biol. Chem.*, 264:14256–14261, 1989.

Vestweber and Schatz, "DNA–protein conjugates can enter mitochondria via the import pathway," *Nature*, 338:170–172, 1989.

Wales et al., "Addition of an ER retention signal to the ricin–A chain increases the cytotoxicity of the holotoxin," *Exp. Cell Res.*, 203:1–4, 1992.

Wang et al., "Impaired secretion and fluid–phase endocytosis in the End4 mutant of Chinese hamster ovary cells," *J. Biol. Chem.*, 265:20179–20187, 1990.

Wittung et al., "Phospholipid membrane permeability of peptide nucleic acid," *FEBS Letters*, 365:27–29, 1995.

Zhao and London, "Conformation and model membrane interactions of diphtheria toxin fragment A," *J. Biol. Chem.*, 263(30):15369–15377, 1988.

```
     Asp  Cys  Tyr  Ala  Ser  Gln  Pro  Gly  Lys  Pro  Pro  Arg  Glu            SEQ ID NO:4
                                                                                 SEQ ID NO:3
5'   GAC  TGT  TAC  GCC  AGC  CAG  CCC  GGC  AAA  CCA  CCG  CGT  GAG             SEQ ID NO:6
     ACA  ATG  CGG  TCG  GTC  GGG  CCG  TTT  GGT  GCA  CTC  CTG
                                                  DraIII

FIG. 2A

AvaII
                                            ↓
     Tyr  Ala  Ser  Gln  Pro  Gly  Lys  Pro  Pro  Arg  Glu  Asp  Leu  Lys        SEQ ID NO:5
                                                                                 SEQ ID NO:7
5'   TAC  GCC  AGC  CAG  CCC  GGC  AAA  CCG  CCG  CGC  GAG  GAC  CTG  AAG
                              605                     610            613

FIG. 2B

Tyr  Ala  Ser  Gln  Pro  Gly  Lys  Pro  Pro  Arg  Glu  Asp  Cys  Tyr        SEQ ID NO:9
                                                                                 SEQ ID NO:8
5'   TAC  GCC  AGC  CAG  CCC  GGC  AAA  CCG  CCG  CGC  GAG  GAC  TGT  TAC
     600                                                 610          612

Ala  Ser  Gln  Pro  Gly  Lys  Pro  Pro  Arg  Glu  Asp  Leu  Lys             SEQ ID NO:9(cont.)
                                                                                 SEQ ID NO:8(cont.)
     GCC  AGC  CAG  CCC  GGC  AAA  CCA  CCG  CGT  GAG  GAC  CTG  AAG  TAA
     615                           620                      625
                                        DraIII

METHODS AND COMPOSITIONS FOR USING MEMBRANE-PENETRATING PROTEINS TO CARRY MATERIALS ACROSS CELL MEMBRANES

The present application is a continuation in part of U.S. Provisional Patent Application 60/042,056, filed Mar. 26, 1997 to which applicants claim priority under 35 U.S.C. 119 (e). The entire text of this prior disclosure is incorporated herein by reference.

The government may own certain rights in the present invention pursuant to grant number GM 43612 from the National Institutes of Health.

BACKGROUND OF THE INVENTION

1. Field of the Invention

The present invention relates generally to the fields of cell biology and drug delivery. Particularly, it concerns the use of inactivated or modified toxins to deliver drugs to the cytoplasm of target cells

2. Description of Related Art

New therapies are under development that seek to address diseased states at the molecular level. A major problem in the practical application of many new therapeutic agents is that the agents do not readily cross cellular membranes and thus cannot reach compartments within the cell where their sites of action may reside. There are numerous reasons why agents are unable to penetrate cell membranes including the intrinsic charge, size, and chemical composition of the agents. Potentially therapeutic molecules such as nucleic acids, oligonucleotides, proteins, peptides and other related agents, as well as a small organic compounds, are subject to these limitations.

Prior art methods facilitate the passage of some of these agents across membranes, but the methods are usually not highly efficient nor are they readily applied to an intact organism, or both. Moreover, they are not usually able to deliver material selectively to a desired cell type by specifically binding to features of the desired target cell. For example, the passage of nucleic acids across a membrane and into cells can be facilitated by methods such as electroporation, calcium phosphate precipitation, and liposome-mediated transfection and attachment to facilitating peptides. These methods often are membrane disruptive and damage cells, limiting their effectiveness in vivo, or are not able to specifically deliver to desired target cells.

SUMMARY OF THE INVENTION

It is, therefore, an object of the present invention, to provide compositions and methods for the transfers of various molecules across biological membranes. A variety of different uses for these compositions and methods are contemplated, as described further below.

In one embodiment, there is provided a method of providing a molecule to a cell comprising (i) conjugating said molecule to a detoxified exotoxin A (ETA) at a non-terminal site; and (ii) contacting the conjugate with said cell, whereby said conjugate is delivered to the cytoplasm of said cell. The molecule may be a nucleic acid, a peptide, a peptide-nucleic acid, an antibody, a single-chain antibody or a pharmaceutical. The antibody or single-chain antibody may be ones that have catalytic function. The nucleic acid may be DNA o RNA. Where a DNA is involved, it may be placed under the control of a eukaryotic promoter. The DNA may encode a nucleic acid binding protein, a single-chain antibody, a tumor suppressor, a cytokine, an oncogene, a hormone or a toxin. The promoter may be a CMV IE, β-actin, E1A, TET or ecdysone. The DNA may encode an antisense construct, for example, an antisense construct that targets an oncogene or a viral protein. The polypeptide may be an enzyme, an antibody or a nucleic acid binding protein.

Various methods of conjugation are contemplated, for example, by a covalent bond or non-covalent. The bond may be reducible. The bond may be a carbon-sulfur bond, carbon-carbon bond, carbon-oxygen bond or a carbon-nitrogen bond. The sulfur residue of said carbon-sulfur bond may be a component of said detoxified ETA.

The detoxified ETA may be produced recombinantly. The detoxified ETA may contain a sulfur residue not found in the natural toxin. The detoxified ETA may contain a deletion, insertion or substitution in domain III. The detoxified ETA may contain a deletion of the glutamate residue at position 553 of the natural toxin.

Provision of the conjugate to a cell may be performed in vitro or in vivo. Exemplary cells include a CHO cell, a CV-1 cell, a Vero cell, an embryonic stem cell, a HeLa cell, a smooth muscle cell, a fibroblast, a tumor cell, a B-lymphocyte or a T-lymphocyte.

In another embodiment, there is provided a conjugate comprising (i) a detoxified ETA; and (ii) another molecule conjugated to said detoxified ETA at a non-terminal site. The molecule may be a nucleic acid, a peptide, a peptide-nucleic acid, an antibody, a single-chain antibody or a pharmaceutical. The antibody or single-chain antibody may be ones that have catalytic function. The nucleic acid may be DNA o RNA. Where a DNA is involved, it may be placed under the control of a eukaryotic promoter. The DNA may encode a nucleic acid binding protein, a single-chain antibody, a tumor suppressor, a cytokine, an oncogene, a hormone or a toxin. The promoter may be a CMV IE, β-actin, E1A, TET or ecdysone. The DNA may encode an antisense construct, for example, an antisense construct that targets an oncogene or a viral protein. The polypeptide may be an enzyme, an antibody or a nucleic acid binding protein.

In yet another embodiment, there is provided a pharmaceutical composition comprising (i) an ETA conjugate comprising (a) a detoxified ETA, (b) another molecule conjugated to said detoxified ETA at a non-terminal site; and (ii) a pharmaceutically acceptable buffer diluent or excipient. The molecule of the pharmaceutical composition may be a nucleic acid, a peptide, a peptide-nucleic acid, an antibody, a single-chain antibody or a pharmaceutical.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A, FIG. 2B and FIG. 2C. The insertion of DNA encoding a cysteine residue into the structural gene for ETA. The strategy for placing a cysteine residue in the carboxyl-terminal region of ETA inserts a linker encoding cysteine at the AvaII site (nucleotide 2649) near the end of the coding sequence. FIG. 2A (SEQ ID NO:3, SEQ ID NO:4, SEQ ID NO:6) shows the sequence of the synthetic double stranded linker, the overhangs at the ends (italics) complement the overhangs of AvaII digestion sites. The Cys residue and its codon are in bold and the unique DraIII site is underlined. FIG. 2B shows the sequence around the AvaII site in wild-type ETA (SEQ ID NO:5, SEQ ID NO:7). The AvaII site where the linker in FIG. 2A is inserted is underlined and the cleavage point is indicated by the arrow. FIG. 2C (SEQ ID NO:8, SEQ ID NO:9) indicates the final sequence after insertion of the linker at the AvaII site. Amino acids encoded by the insert are in bold print. The DraIII site engineered into the linker is unique and facilitates identification of plasmids carrying the insert. Numbers beneath sequences refer to amino acids in ETA.

FIG. 4A shows the purification of ETA-ΩCys612-PNA from unreacted PNA and ETA-ΩCys612 upon elution from an anion exchange column by a linear salt gradient. FIG. 4B shows the purity of the eluted material by electrophoretic analysis on a non-denaturing polyacrylamide gel.

DESCRIPTION OF ILLUSTRATIVE EMBODIMENTS

Figure 1:
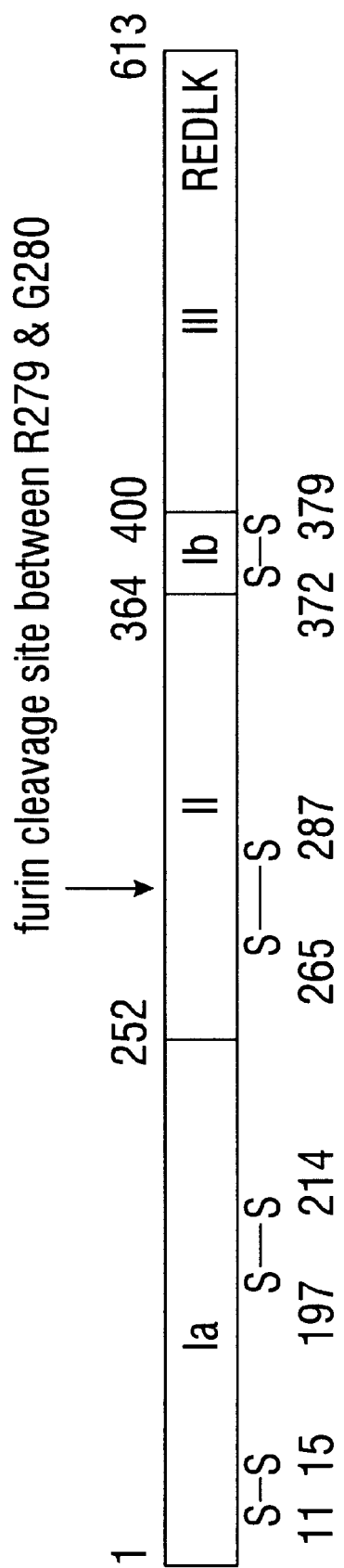
FIG. 1. Structural features of ETA. The boxed areas represent the mature protein from amino acids 1 to 613. The domains are indicated within the boxed areas and the amino acid numbers dividing the domains are shown above the boxes. The REDLK (SEQ ID NO:10) sequence at the C-terminus, of which REDL (SEQ ID NO:11) is required for cytotoxic activity, is shown in the boxed area of domain III. Disulfide bonds are indicated below the boxed areas and the numbers refer to the cysteine residues participating in the disulfide bonds. The location of the furin cleavage site is indicated by the arrow.
Figure 3:
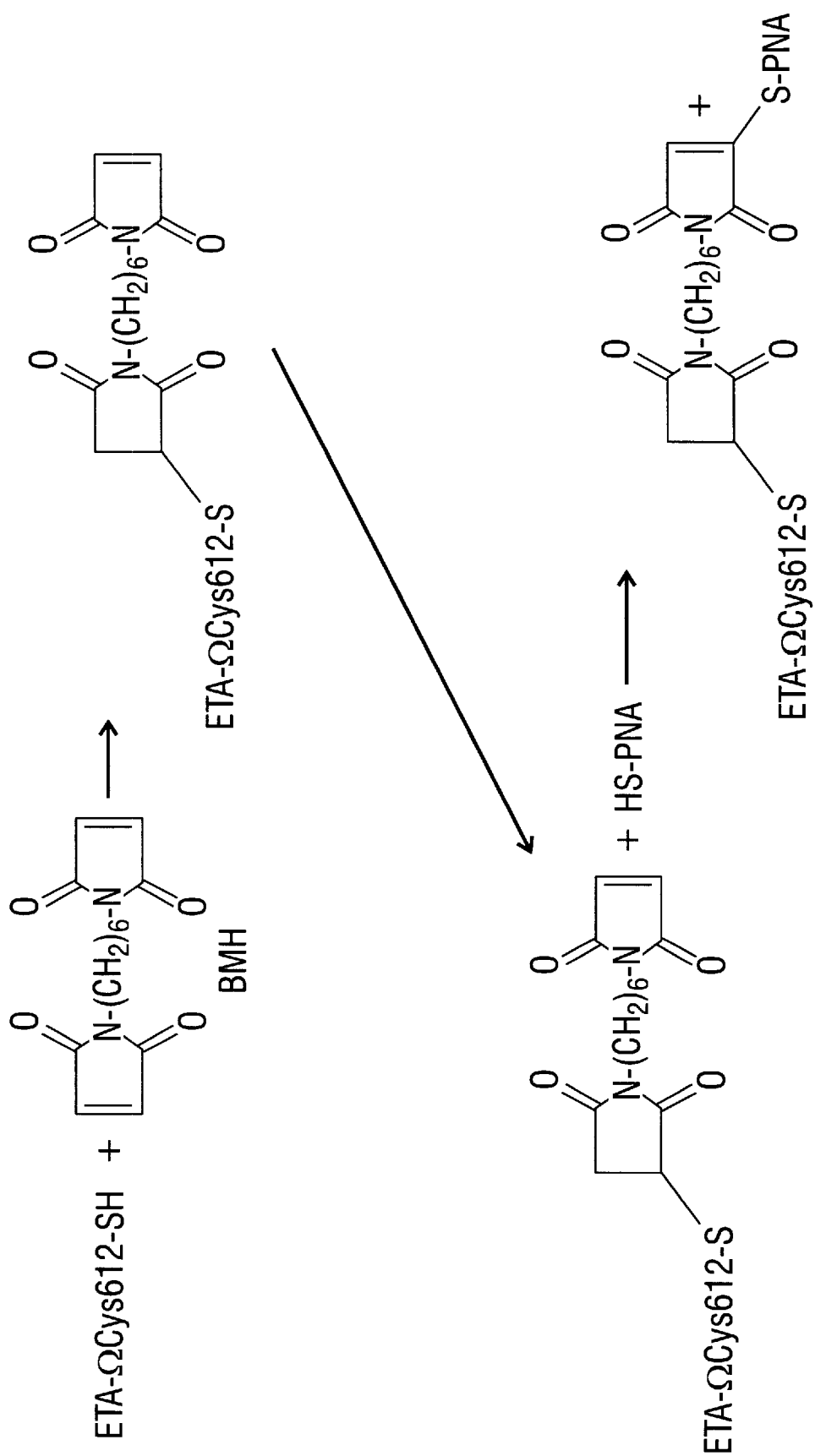
FIG. 3. Attachment of ETA to a PNA using the cross-linker BMH. Step 1 shows the reaction of ETA-ΩCys612 (5) with Bismaleimidohexane (BMH, (2)) to yield ETA-Ω Cys612-BMH (6). Step 2 shows the reaction of ETA-ΩCys612-BMH with SH-PNA to yield the PNA-ETA conjugate (7).

Over recent years, an immense increase in the understanding of disease has been obtained at the molecular level. Thus, in many cases, there have been presented new and exciting opportunities to intervene at the molecular basis for disease. One of the major hurdles with such approaches involves how to effectively and selectively transport the therapeutic agent—a protein, a gene, or other drug—into the affected cell where the site of action lies. While a number of different approaches have been attempted, the cellular membrane remains, both literally and figuratively, a formidable barrier to success in this area.

In this regard, there are certain proteins that have the advantageous property of being able to pass through membranes into cells. Moreover, the proteins bind to receptors as a prerequisite for passing through a membrane which offers the opportunity to target only cells that have the receptors. These proteins, which will be termed hereafter as membrane-penetrating proteins (MPPs), include, but are not limited to, several plant and bacterial protein toxins, such as ricin, abrin, modeccin, diphtheria toxin, cholera toxin, anthrax toxin, heat labile toxins, and *Pseudomonas aeruginosa* exotoxin A (ETA). Examples of proteins that are not toxins but which appear to have properties of an MPP, include the TAT protein of human immunodeficiency virus (Frankel and Pabo, 1988; Mann and Frankel 1991) and the protein VP22, the product of the UL49 gene of herpes simplex virus type 1. One line of research involves adapting such molecules from their naturally destructive role into therapeutic compositions. If this can be accomplished, nature may have already provided a valuable starting point for the improvement of molecular therapies.

Clearly, one large problem with the use of toxins in therapy is their inherent toxic nature. With an improved understanding of the molecular basis for toxicity, however, it is possible that the advantageous aspects of toxins (i.e., membrane penetration) can be retained while eliminating the undesirable toxicity. With ETA, for example, there is information on the regions of the molecule that are involved with transport and toxicity. One study has demonstrated that relatively minor changes to domain III can greatly reduce toxicity (Benhar et al., 1994). Other studies have showed that chimeric proteins having domain III of ETA replaced with another protein still could be transported into cells (Pastan and FitzGerald, 1991; Pastan et al., 1992).

The current hypothesis for the action of MPP's is that these molecules use pores in the hydrophobic lipid bilayer. These pores may be pre-existing in the bilayer or may be formed by the toxin itself. With respect to ETA, the work of Pastan et al., as discussed above, provides important information on what regions of ETA are involved in the various activities (transport, toxicity) of this molecule. However, it does not fully address what kind of modifications ETA can tolerate while retaining its ability to use a pore and translocate to the cytoplasm of a cell. In particular, these studies on protein chimeras do not answer the question of whether other agents, including non-protein molecules, can be conjugated to various non-terminal regions of a toxin, thereby effectively generating branched structures, without impeding transfer of the conjugate into the cytoplasm. Given the steric and hydrophobic-hydrophilic factors that affect pore formation, even relatively subtle changes in a molecule can have dramatic effects. It even is true that subtle changes (e.g., substitutions) could potentially have more dramatic effects than wholesale deletions or replacements.

The present invention employs a group of proteins known as membrane penetrating proteins, of which ETA is an example, to carry a variety therapeutic agents across the cellular membrane and into the cytoplasm. There are multiple advantages to such a technique, including decreased doses of therapeutic agents, effective targeting of an agent to a specific point within a cell, and reduced toxicity due to the use of lower doses. Based on the work of the present inventors, it has been established that certain non-terminal conjugates of ETA, specifically peptide-nucleic acids, can be transported into the cytoplasm of cells.

In one embodiment, the present invention employs an enzymatically inactivated ETA, an exemplary MPP, that contains a non-terminal chemical binding site to which a therapeutic agent of choice may be attached to facilitate the transport of the agent across a membrane into the cell cytoplasm. An "agent" as defined herein is any molecule that is to be transported across a membrane by the ETA compositions of the present invention. Examples of the agent of choice include but are not limited to proteins that express an enzymatic activity, for example, ricin-A, which has an activity that will kill cells; p53, which may have anticancer activity in some cells; forms of ras, which may intercede in signaling pathways to reduce the growth of some tumor cells. The agent of choice could also include, proteins that bind to targets inside the cell. Examples of such binding proteins are an antibody or part of an antibody that binds a desired target in the cell; a DNA binding protein that may react with DNA and modify the expression of genes; an RNA binding protein that may bind to RNA and modulate the synthesis of a protein.

The present invention also can be employed to transfer non-terminally bound peptide or drug, a part of which is a peptide, into the cytoplasm of cells by attachment to an MPP. As employed herein the term non-terminal is used to indicate a region of an MPP that is flanked on either side by other MPP sequences. Examples of such peptides include, but are not limited to, use of peptides that interact with cellular proteins; peptides that interact with DNA or RNA; peptides that interact with carbohydrates or other natural cellular substances. In another example, a DNA, an RNA or a peptide nucleic acid, or a synthetically altered nucleic acid, such a phosphorothioate or methylated DNA or RNA, may be attached to an MPP to facilitate the passage of the agent across a membrane. Examples include, but are not limited to, DNA encoding genes; antisense oligonucleotides of any kind; RNA molecules that have been engineered to contain a binding or enzymatic activity. In yet another example, the attached agent may be any organic compound that has therapeutic potential if the effectiveness of the drug could be enhanced by facilitating passage of the drug through a membrane and into a target cell. Examples include, but are not limited to, drugs that may have anti-tumor activity; drugs that my inhibit or enhance the activity of a natural substance, such as a protein or nucleic acid, already in the cell; drugs that may have a protective effect on cellular activity by adsorbing harmful chemicals or radiation.

Thus, the present invention describes the conjugation of the aforementioned groups of compounds to an MPP so that they can be therapeutically transferred into cell cytoplasm. It is contemplated that any membrane penetrating protein may be employed in the present invention. As detailed here, ETA has been employed as an exemplary MPP of the present invention. The methods and composition for using MPPs to facilitate the transport of agents into the cytoplasm of cells are described in further detail herein below.

1. Exotoxin A

Exotoxin A (ETA) is a virulence factor and protein secreted by the bacteria *Pseudomonas aeruginosa*. ETA is the 66 kD protein product of the *Pseudomonas aeruginosa* toxA gene (SEQ ID NO:2, encoded by SEQ ID NO:1). The mature form of ETA has been subdivided into three domains, the receptor binding domain (domain I, residues 1–252 and 365–404), the membrane penetrating domain (domain II, residues 253–364), and the enzymatic ADP-ribosylation domain (Domain III, residues 405–613). The domains of ETA have been defined by x-ray crystallography (Allured et al. 1986) which shows that the functional domains overlap with the structural domains (FIG. 1).

There are three main steps in the mechanism of ETA action, roughly defined by events occurring in the three domains of the toxin. The first step is binding to a cell surface receptor followed by endocytosis of the toxin. The second step is the penetration of the toxin through a membrane and into the cell cytosol. The third step is the inactivation of protein synthesis by the toxin that has passed through a membrane, which kills the cell. Events occurring in these steps is described in more detail in the following paragraphs.

The cell surface receptor for ETA is the low density lipoprotein receptor-related protein (LDLRRP), a glycoprotein ubiquitously expressed on the surface of eukaryotic cells (Kounnas et al., 1992). The receptor-binding function of ETA has been assigned to domain I (Allured et al., 1986).

Once ETA binds LDLRRP, the complex is internalized by receptor-mediated endocytosis to appear within vesicles in the cell. It is important to note that even though ETA is in vesicles in the cell at this point, it is still separated from the cytoplasm by a membrane barrier, just as if it were still outside the cell. This caveat applies to any material that has been endocytosed: the material still must penetrate a membrane to reach the cytoplasm.

The second step in the mechanism ETA of action, penetration through a membrane, is not well-understood, but there are nevertheless several important facts known about the process. One fact is that ETA must be proteolytically cleaved before passing through a membrane (Ogata et al., 1990, 1992). Cleavage is between Arg279 and Gly280 of domain II, creating an N-terminal polypeptide of about 29 kD and a C-terminal fragment of about 37 kD. The C-terminal polypeptide contains part of domain II and all of domain III and is the part of ETA that is known to pass through a membrane and enter the cytoplasm. Cleavage is effected by the protease furin, a subtilisin-like protease (Gordon and Leppla, 1994). Once cleavage has occurred, the N-terminal and C-terminal fragments remain connected by a disulfide bond, which is reduced at some point during the action of the toxin, but it is not understood exactly how or when reduction takes place.

The action of several drugs on the cytotoxic activity of the of ETA have further provided clues to events that occur during part of the process by which the toxin passes through a membrane. Drugs that elevate the pH within the vacuolar compartment inhibit the entry of ETA into the cytosol, suggesting that the toxin needs to be exposed to a low pH before passing through a membrane. Exposure to a low pH may be needed to cause a conformational change in the toxin that is important for some later step of entry. The identity of the intracellular compartment through whose membrane the toxin actually passes to reach the cytoplasm is not clear. It is known, however, that four of the last five amino acids of ETA (REDLK SEQ ID NO:10) are important in the intracellular transport and cytotoxicity of the protein. Loss of the REDL (SEQ ID NO:11) sequence inhibits the ability of ETA to reach the cytoplasm. However, REDL (SEQ ID NO:11) can be substituted with another sequence, KDEL (SEQ ID NO:12), without loss of cytotoxicity (Chaudhary et al., 1990). KDEL (SEQ ID NO:12) is the consensus intracellular transport signal used for returning back to the endoplasmic reticulum (ER) proteins that have escaped from the ER and entered the Golgi complex. The mechanism involves a receptor called the KDEL (SEQ ID NO:12) receptor whose function is to transport proteins containing the KDEL (SEQ ID NO:12) sequence from the Golgi apparatus to the ER. This has lead to the suggestion that ETA interacts with the KDEL (SEQ ID NO:12) receptor and that ETA may reach the interior of the ER before penetrating to the cytosol through the ER membrane (Pastan et al., 1992; Pelham et al., 1992). In support of the idea that ETA enters the ER en route to the cytoplasm is the observation that brefeldin A inhibits the appearance of ETA in the cytoplasm (Hudson and Grillo, 1991). Brefeldin A is known to disrupt the Golgi and should also disrupt access to the ER, thus inhibiting the entry of the toxin into the cytoplasm. However, there is as yet no direct demonstration that ETA physically enters the ER at any time.

The third step in the mechanism of ETA action, inhibition of protein synthesis, is well-understood. Domain III carries an enzymatic activity that transfers the ADP-ribosyl moiety of NAD to elongation factor 2 (EF-2), which inactivates EF-2 and arrests protein synthesis. It should be noted for purposes of this invention, however, that modification of the catalytic center by recombinant DNA techniques can produce a form of ETA that has no catalytic activity and which is therefore not poisonous to the cell (Lukac et al., 1988). It is this modified form which can be used as the vehicle to carry material across membranes so that there is no harm to the cell by ETA itself.

2. Modifications of ETA

The present invention may be used to transport a variety of compounds across a membrane and into the cell cytoplasm by using an MPP carrier. In a particular example of such transport, PNAs are transported into the cytoplasm. However, it will be appreciated that one of skill in the art may employ the present invention to transport any peptide or other molecule, that lends itself to conjugation with an MPP, across the membrane and into the cytoplasm where such a molecule may exert its effect.

In the present invention the MPP carrier is a modified form of ETA. The modifications to the ETA are two fold. The first modification results in a modified ETA molecule that has a reduced cytotoxicity. The second modification to the ETA is in domain III of the ETA molecule which allows for the covalent linking of agents to the ETA to facilitate the transport of the agents into the cytoplasm of a cell. These modification are discussed in further detail herein below.

a. Reduction of ETA Cytotoxicity

In order to employ ETA to transport molecules into the cytoplasm without ETA killing the cell it is necessary to diminish the cytotoxicity of the wild-type ETA molecule. This may be achieved by mutating the active site of the protein so that its cytotoxic effect will not manifest. The catalytic domain of ETA (Domain III) shows sequence homology to the catalytic fragment of diphtheria toxin (Zhao and London, 1988), which catalyzes the transfer of the ADP-ribosyl moiety of NAD to elongation factor-2 (EF-2). This inactivates EF-2 and thereby inhibits protein synthesis.

In the present invention, the enzymatic activity of ETA has been eliminated by the deletion of a glutamate residue in the active site of domain III at position 553. The resulting material is called ETA-ΔGlu553. This modification is well-known in the art as described by Lukac et al. (1988). There are many other ways one skilled in the art could inactivate the enzymatic activity of ETA, and other MPPs, to render them innocuous to the cell (should they have an activity deleterious to the cell), thereby creating a neutral carrier MPP that itself will have minimal impact on the physiology of the target cell. The use ETA with glutamate 553 deleted should in no way be construed as a limit on the use of other methods to inactivate MPPs for use in this invention. Such methods are discussed in further detail below.

b. Modification of ETA to Permit Branched Coupling

The second modification to ETA allows for the conjugation of agents to the ETA at a non-terminal location of the ETA molecule. This modification is exemplified by, but by no means limited to, the introduction, using recombinant DNA techniques, of a free cysteine in domain III of ETA that serves as a site to covalently couple agents to ETA.

A cysteine residue was inserted at position 612 near the carboxyl terminus of ETA to provide a free reactive sulfhydryl group as a convenient site to attach agents to be transported by ETA. The method for inserting the cysteine is described in FIG. 2 and involved duplicating a 13-residue peptide normally present in the toxin, recreating the REDLK sequence (SEQ ID NO:10) at the carboxyl end that is necessary for transport to the cytoplasm. The last 13 residues of ETA are unstructured in the crystal structure, suggesting that they are flexible (Allured et al., 1986).

The cysteine was inserted as part of a duplication of this flexible 13-residue sequence to improve the chances that it would be reactive in conjugation reactions. This variant of ETA is called ETA-ΩCys612 to denote the insertion of cysteine at position 612. Briefly, the strategy for placing a cysteine residue in the carboxyl-terminal region of ETA inserts a linker encoding cysteine at the AvaII site (nucleotide 2649) near the end of the coding sequence. The sequence of the synthetic double stranded linker the inventors used is shown in FIG. 2A. The overhangs at the ends (italics) complement the overhangs of AvaII digestion sites. The Cys residue and its codon are in bold and the unique DraIII site is underlined. The 5' end of the linker encodes an Asp that regenerates the Asp codon at the AvaII site of insertion. The desired cysteine residue is carboxyl-terminal to the Asp and the rest of the linker duplicates the amino acid sequence from residues 600 to 610 in ETA. This scheme retains the REDLK (SEQ ID NO:10) sequence at the carboxyl terminus of the protein. The sequence around the AvaII site in wild-type ETA is shown in FIG. 2B. The AvaII site where the linker in FIG. 2A is inserted is underlined and the cleavage point is indicated by the arrow. The final sequence after insertion of the linker at the AvaII site is indicated in FIG. 2C. Amino acids encoded by the insert are in bold print. This construct has the advantage that it extends the REDLK sequence (SEQ ID NO:10) away from the cysteine site to avoid interference of adducts conjugated to cysteine with the REDLK sequence (SEQ ID NO:10). The DraIII site engineered into the linker is unique and facilitated identifying plasmids carrying the insert. Numbers beneath sequences refer to amino acids in ETA.

It is an important inventive feature that this cysteine is in the 37 kDa furin fragment of ETA that is known to pass through a membrane and enter the cytoplasm. Thus although in preferred embodiments the cysteine residue is inserted at position 612 it is contemplated that the cysteine residue may be inserted at any site in the furin fragment of ETA so long as the residue is free to be conjugated to agents to be transported into the cytoplasm. Thus, agents attached to this cysteine would have the opportunity to be carried into the cytoplasm.

It will be appreciated by those skilled in the art that the essence taught by this invention is that an agent attached to an MPP will be carried across a membrane, and that there are many ways one skilled in the art may attach agents to an MPP, including but not limited to attachment at cysteine residues as taught in this embodiment. While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention.

3. Assaying and Screening for ETA Activity

The enzymatic, cytotoxic and membrane penetrating activities of ETA and any modified ETA may be measured using assays well known to those of skill in the art. Enzymatic activity assays have been described by Iglewski and Sadoff (1979). Briefly, activated toxin is incubated with $^{14}$C-NAD$^+$ and wheat germ EF-2, and the ETA-catalyzed transfer of radioactivity to the TCA-precipitable material is measured. Activity is then be compared to that of wild type toxin.

The cytotoxic activity is tested by inhibition of protein synthesis as described by Chaudhary et al., (1989). Sensitive cells are incubated with varying concentrations of toxin at physiological temperature, and protein synthesis is measured as the incorporation of $^{35}$S-Met into TCA-precipitable material. The common assessment of cytotoxicity is the $ID_{50}$, the concentration of toxin required to reduce protein synthesis by 50%. Again, the activity ($ID_{50}$) will be compared to wild type toxin.

Within certain embodiments of the invention, methods are provided for screening for modified ETA molecules that do not exhibit the cytotoxic capacity of wild-type ETA. Such methods may use ADP-ribosylation assay, NAD-glycohydrolase and cytotoxicity assays (Douglas and Collier, 1987; Douglas et al., 1987) to screen and identify modified ETA molecules.

Where transportation capabilities of the modified ETA molecule are to be tested the compound being transported may be labeled in such a way as to make it amenable to detection, for example, radiolabeled, fluorescently labeled or perhaps being detectable by an antibody. Thus the transport of the molecule may be tested by fractionating the cell to determine whether the labeled fraction is in the membrane fraction or in the soluble fraction. If the label appears in the soluble fraction it will be indicative of the modified ETA being useful as a transporter of that particular compound. Such assays are well known to those of skill in the art and are easy to set up.

Within one example, a screening assay is performed in which cells are exposed to a modified ETA under suitable conditions and for a time sufficient to permit the agent to have a cytotoxic effect on the cell. The cytotoxic effect of a modified ETA is then detected by incubating the reaction mixture as described by Chaudhary et al., (1989) under conditions that permit the formation of the cytotoxic effect. The test reaction is compared to a control reaction which contains wild-type ETA. To complete the screening assay, the presence and/or amount of cytotoxic response is detected in the test. Within this exemplary assay, modified ETAs that have a reduced cytotoxic capacity demonstrate a reduction in cytotoxic effect in the cells being tested as compared to wild-type ETA.

In these embodiments, the present invention is directed to a method for determining the ability of a modified ETA to exhibit reduced cytotoxicity as compared to wild-type ETA such a method including generally the steps of:

(a) obtaining a cell capable of have a cytotoxic response to ETA (b) admixing a modified ETA with the cell; and (c) determining the ability of the modified ETA to have a cytotoxic effect on the cell.

To identify a candidate substance as being capable of having a reduced cytotoxic effect in comparison to wild-type ETA, one would measure or determine such an activity in the presence of ETA. One would then measure the activity in cells to which the candidate substance has been added. A candidate substance which has a decreased cytotoxic effect in comparison to wild-type ETA is indicative of a modified ETA that will be useful in the present invention.

The candidate screening assay is quite simple to set up and perform, and is related in many ways to the assay discussed above for determining the cytotoxic activity of ETA. Thus, after obtaining a cell which exhibits a cytotoxic response to ETA, one will admix a candidate a modified ETA with the cell, under conditions which would allow the cytotoxic responses in the presence of ETA and compare this response to that obtained with the inclusion of a modified ETA. In this fashion, one can measure the ability of the modified ETA to exhibit a decreased cytotoxic response relative to the wild-type ETA.

"Effective amounts" in certain circumstances are those amounts effective to reproducibly decrease the cytotoxic activity, in comparison to the level of cytotoxicity in response to wild-type ETA. Compounds that achieve significant appropriate changes in activity will be used.

Significant decrease in cytotoxic activity levels of at least about 30%–40%, and most preferably, by decreases of at least about 50%, with higher values of course being possible. Assays that measure cytotoxicity of ETA are well known to those of skill in the art (Douglas and Collier, 1987; Douglas et al., 1987) and are discussed elsewhere in the specification.

It will, of course, be understood that all the screening methods of the present invention are useful in themselves notwithstanding the fact that effective candidates may not be found. The invention provides methods for screening for such candidates, not solely methods of finding them.

4. ETA Polypeptide Expression and Modification

In order to generate the modified ETA compositions of the present invention it will be necessary to express the ETA gene. This may be achieved by inserting the ETA gene into an appropriate expression system. The gene can be expressed in any number of different recombinant DNA expression systems to generate large amounts of the polypeptide product, which can then be purified and conjugated to any molecule that is required to be delivered into a cell.

In one embodiment, amino acid sequence variants of the polypeptide can be prepared. These may, for instance, be minor sequence variants of the polypeptide that arise due to natural variation within the population or they may be homologues found in other species. They also may be sequences that do not occur naturally but that are sufficiently similar that they function similarly and/or elicit an immune response that cross-reacts with natural forms of the polypeptide. Sequence variants can be prepared by standard methods of site-directed mutagenesis such as those described below in the following section.

Amino acid sequence variants of the polypeptide can be substitutional, insertional or deletion variants. Deletion variants lack one or more residues of the native protein which are not essential for function or immunogenic activity, and are exemplified by the variants lacking a catalytic function described above.

Substitutional variants typically contain the exchange of one amino acid for another at one or more sites within the protein, and may be designed to modulate one or more properties of the polypeptide such as stability against proteolytic cleavage. Substitutions preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also can include hybrid proteins containing sequences from other proteins and polypeptides which are homologues of the polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptide. These typically are smaller insertions than the fusion proteins described above and are introduced, for example, into a protease cleavage site.

In one embodiment, major antigenic determinants of the polypeptide are identified by an empirical approach in which portions of the gene encoding the polypeptide are expressed in a recombinant host, and the resulting proteins tested for their cytotoxicity. For example, PCR can be used to prepare a range of cDNAs encoding peptides lacking successively longer fragments of the active site or containing mutations at the active site that of the protein that render the protein less cytotoxic than the wild-type protein. The insertion of one or more cysteine residues at the C-terminal of the protein is envisioned in order to make the polypeptide amenable to conjugation to molecules that are to be delivered into the cell of choice. Further experiments in which only a small number of amino acids are removed at each iteration then allows the location of the antigenic determinants of the polypeptide.

Modification and changes may be made in the structure of a gene and still obtain a functional molecule that encodes a protein or polypeptide with desirable characteristics. These characteristics entail the modified ETA molecule being less cytotoxic than the wild-type ETA and yet retaining the translocation capabilities of the wild-type molecule. The following is a discussion based upon changing the amino acids of a protein to create an equivalent, or even an improved, second-generation molecule. The amino acid changes may be achieved by change the codons of the DNA sequence, according to the following data.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982).

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |

TABLE 1-continued

| Amino Acids | | | Codons |
|---|---|---|---|
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Site-Specific Mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement. Thus site directed mutagenesis may be employed to produce sequence variants of ETA in which the enzymatic and cytotoxic activity of the protein are reduced (Lukac and Collier, 1988; Douglas and Collier, 1987).

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

5. Expression Constructs

Expression constructs are important to the instant application for two reasons. First, production of ETA for conjugation to various agents, as described briefly above, is advantageously accomplished by expressing a cloned ETA gene in vitro. Second, the agent conjugated to ETA may, in fact, be an expression construct that, when transported into a cell, permits the production of a protein, antisense molecule or ribozyme. These embodiments are discussed in greater detail below.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of an mRNA into a protein product. In other embodiments, expression only includes transcription of the nucleic acid encoding a gene or its complement, i.e., and antisense or ribozyme molecule.

In order for the construct to effect expression of a gene of interest, the polynucleotide encoding the polypeptide will be under the transcriptional control of a promoter. A "promoter" refers to a DNA sequence recognized by the synthetic machinery of the host cell, or introduced synthetic machinery, that is required to initiate the specific transcription of a gene. The phrase "under transcriptional control" means that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a polynucleotide is not believed to be critical, so long as it is capable of expressing the polynucleotide in the targeted cell at sufficient levels. Thus, where a human cell is targeted, it is preferable to position the polynucleotide coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of the polynucleotide. The use of other viral or mammalian cellular or bacterial phage promoters which are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter which is active in specific cells, such as tyrosinase (melanoma), alpha-fetoprotein and albumin (liver tumors), CC10 (lung tumor) and prostate-specific antigen (prostate tumor) will permit tissue-specific expression of ETA polynucleotides. Table 2 lists several elements/promoters which may be employed, in the context of the present invention, to regulate the expression of constructs. This list is not intended to be exhaustive of all the possible elements involved in the promotion of ETA expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

TABLE 2

| ENHANCER |
|---|
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| $α_1$-Antitrypsin |
| H2B (TH2B) Histone |

TABLE 2-continued

| ENHANCER |
|---|
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

Further, selection of a promoter that is regulated in response to specific physiologic signals can permit inducible expression of the genetic construct. For example, with the polynucleotide under the control of the human PAI-1 promoter, expression is inducible by tumor necrosis factor. Table 3 illustrates several promoter/inducer combinations:

TABLE 3

| Element | Inducer |
|---|---|
| MT II | Phorbol Ester (TFA) Heavy metals |
| MMTV (mouse mammary tumor virus) | Glucocorticoids |
| β-Interferon | poly(rI)X poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |

In certain embodiments of the invention, the delivery of an expression vector in a cell may be identified in vitro or in vivo by including a marker in the expression vector. The marker would result in an identifiable change to the transfected cell permitting easy identification of expression. Usually the inclusion of a drug selection marker aids in cloning and in the selection of transformants. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed along with the polynucleotide encoding ETA. Further examples of selectable markers are well known to one of skill in the art.

One typically will include a polyadenylation signal to effect proper polyadenylation of the transcript. The nature of the polyadenylation signal is not believed to be crucial to the successful practice of the invention, and any such sequence may be employed. The inventor has employed the SV40 polyadenylation signal in that it was convenient and known to function well in the target cells employed. Also contemplated as an element of the expression construct is a terminator. These elements can serve to enhance message levels and to minimize read through from the construct into other sequences.

6. Agents Attached to ETA

A variety of agents may be transported into the cell cytoplasm using the present invention including proteins, PNAs, drugs, antisense molecules, ribozymes, single chain and monoclonal antibodies. These agents are discussed in further detail below.

a. Proteins

Proteins that may be transported include p53, ras, single chain antibodies, kinases, phosphatases, nucleases or any other protein that may have an effect within the cytosol of a particular cell.

Thus particular embodiments contemplate the transfer of p53. p53 currently is recognized as a tumor suppressor gene. It is mutated in over 50% of human NSCLC (Hollstein et al., 1991) and in a wide spectrum of other tumors. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or indirectly activate genes that suppress this growth. Thus, the present invention provides methods of delivering such wild-type p53 to a cell in need thereof.

Other proteins contemplated for transfer using the present invention includes p16$^{INK4}$ that has been biochemically characterized as a protein that specifically binds to and inhibits CDK4, and thus may regulate Rb phosphorylation (Serrano et al., 1993; Serrano et al., 1995). p16$^{INK4}$ belongs to a class of CDK-inhibitory proteins that also includes p15$^{INK4B}$, p21$^{WAF1}$, and p27$^{KIP1}$, these may also be conjugated to the MPP compositions described herein. Other examples of proteins to be transferred include C-CAM which is expressed in virtually all epithelial cells (Odin and Obrink, 1987); carcinoembryonic antigen (Lin and Guidotti, 1989).

Other tumor suppressors that may be employed according to the present invention include p21, p15, BRCA1, BRCA2, IRF-1, PTEN, RB, APC, DCC, NF-1, NF-2, WT-1, MEN-I, MEN-II, zac1, p73, VHL, MMAC1, FCC and MCC.

Various enzymes also are of interest according to the present invention. Such enzymes include cytosine deaminase, adenosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase and human thymidine kinase.

Another class of proteins that is contemplated to be delivered using the present invention include interleukins and cytokines. These include but are not limited to interleukin 1 (IL-1), IL-2, IL-3 IL4, IL-5, IL-6, IL-7, IL-8, IL-9, IL-10, IL-11, IL-12, IL-13, IL-14, IL-15, β-interferon, α-interferon, γ-interferon, angiostatin, thrombospondin, endostatin, METH-1, METH-2, GM-CSF, G-CSF, M-CSF and tumor necrosis factor.

Cell cycle regulators may also be provided using the present invention. Such cell cycle regulators include p27, p16, p21, p57, p18, p73, p19, p15, E2F-1, E2F-2, E2F-3, p107 p130 and E2F-4.

Various toxins are also contemplated to be useful as part of the expression vectors of the present invention, these toxins include bacterial toxins such as ricin A-chain (Burbage, 1997), diphtheria toxin A (Massuda et al., 1997; Lidor, 1997), pertussis toxin A subunit, *E. coli* enterotoxin toxin A subunit, cholera toxin A subunit and pseudomonas toxin c-terminal. Recently, it was demonstrated that transfection of a plasmid containing the fusion protein regulatable diphtheria toxin A chain was cytotoxic for cancer cells. Thus, transfer of regulated toxin proteins might also be applied to the treatment of cancers (Massuda et al., 1997).

b. Peptide Nucleic Acids

As an example the present invention is employed to transport peptide nucleic acids into the cytoplasm of a cell. Peptide nucleic acids (PNAs) are DNA/RNA mimics that contain the 4 conventional bases attached to a polypeptide-like backbone rather than to a deoxyribosyl phosphate backbone. A DNA/RNA mimic is a synthetic molecule designed to present relevant structural features of DNA/RNA in an array such that the potential functional properties of such a DNA/RNA molecule are mimicked.

PNAs have a 50-fold to 100-fold higher affinity for complementary RNA and DNA than do conventional oligonucleotides with the same number of bases (Nielsen et al., 1991; Hanvey et al., 1992). PNAs are also very stable in cell extracts and are not degraded when injected into animals (Demidov et al., 1994). These properties make PNAs extremely attractive as antisense therapeutic agents; however, PNAs do not readily cross membrane barriers, which prevents them from reaching intracellular sites of action unaided (Wittung et al., 1995). Therefore, a PNA is attached to a form ETA and carried into the cytoplasm.

c. Drugs

In other embodiments it is anticipated that the present invention will be employed to transfer a variety of drugs into the cytosol of cells. It will be apparent to one of skill in the art that the delivery of a therapeutic drug may be achieved using the present invention. The skilled artisan is referred to "Remington's Pharmaceutical Sciences" 15th Edition, for a comprehensive index of drugs that may be employed. Such drugs include derivatives of natural compounds like carbohydrates, amino acids or nucleic acids that react with cellular enzymes but which cross membranes poorly. Totally synthetic drugs that cross membranes poorly would also be candidates.

d. Antisense Molecules

The present invention may be used to block the production of endogenous protein, one such method involves antisense technology. As stated earlier there is often a problem with delivering a nucleotide molecule into a cell, thus the use of the modified ETA compositions of the present invention will provide a method of delivering therapeutic antisense constructs to a cell.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

Particular oncogenes that are targets for antisense constructs are ras, myc, neu, raf, erb, src, fms, jun, trk, ret, hst, gsp, bcl-2 and abl. Also contemplated to be useful will be anti-apoptotic genes and angiogenesis promoters.

e. Ribozymes

The present invention further contemplates the delivery of ribozymes to a cell in order to block endogenous protein production. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

f. Antibodies

In another aspect, the present invention contemplates the transfer of an antibody into a cell using the methods of the present invention. An antibody can be a polyclonal or a monoclonal antibody. In a preferred embodiment, an antibody is a monoclonal antibody. Means for preparing and characterizing antibodies are well known in the art (see, e.g., Harlow and Lane, 1988).

Briefly, a polyclonal antibody is prepared by immunizing an animal with an immunogen and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. An antigenic composition can be used to immunize one or more experimental animals, which can then proceed to produce specific antibodies. Polyclonal antisera may be obtained, after allowing time for antibody generation, simply by bleeding the animal and preparing serum samples from the whole blood.

As is well known in the art, a given composition may vary in its immunogenicity. It is often necessary therefore to boost the host immune system, as may be achieved by coupling a peptide or polypeptide immunogen to a carrier. Exemplary carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

The immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies depending upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, OF, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. MAbs produced by either means may be further purified, if desired, using filtration, centrifugation and various chromatographic methods such as HPLC or affinity chromatography.

Single chain antibodies, synthesized by the cell and targeted to a particular cellular compartment can be used to interfere in a highly specific manner with cell growth and metabolism. Recent application include the phenotypic knockout of growth factor receptors, the functional inactivation of p21 and the inhibition of HIV-1 replication.

Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (Fvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

In principle, the high affinity and selective binding properties of intracellular antibodies or intrabodies can be used to modulate cellular physiology and metabolism by a wide variety of mechanisms. For example binding of an intrabody may be used to block or stabilize macromolecular interactions, modulate enzyme function by occluding an active site, sequestering substrate or fixing the enzyme in an active or an inactive conformation as the need may be. Intrabodies may also be used to divert proteins from their usual cellular compartment for example by sequestering transcription factors in the cytoplasm, or by retention in the ER of the proteins destined for the cell surface. In this regard intrabodies may be useful in conjunction with the present invention to prevent the cytotoxic effects of ETA being manifested in the host.

Antibodies produced by the methods described above may then be conjugated with toxin of the present invention for delivery into the cytoplasm of a cell as described elsewhere in the specification.

7. Conjugation Techniques

The present invention employs modified ETA molecules that have been constructed to eliminate or reduce the cytotoxic activity of ETA and to add a cysteine residue at the carboxy terminus of the molecule that makes the molecule amenable to attachment of molecules to be transported into the cell. In the various embodiments of the present invention, any of the agents to be delivered into the cytoplasm may be attached to the modified ETA by a covalent linkage. A covalent bond is a chemical linkage in which each atom of a bound pair contributes one electron to form a pair of electrons in a chemical bond. Examples of such attachments or linkages include, but are not limited to, thioether bonds, thioester bonds, carbon-carbon bonds, carbon-oxygen bonds, and carbon-nitrogen bonds. In other examples, the agents may be attached by non-covalent bonds. Examples include, but are not limited to, attachment by ionic bonds, hydrophobic bonds, strong non-covalent interactions such as exist between biotin and an avidin and bonds between an antibody and antigen, and bonds between complementary oligonucleotides. An example of the latter would be the covalent attachment of an oligonucleotide to an MPP, followed by addition of another oligonucleotide part of which contained sequences complementary to the oligonucleotide that was attached to the MPP.

The attachment methods that may be employed in the present invention are well-known in the art. One exemplary method is via the cross linker bismaleimidohexane (BMH), a homobifunctional crosslinker that reacts with free sulfydryl groups to form thioether bonds. The thioether bonds used to attach a PNA to ETA-ΔGlu553-ΩCys612 in this embodiment are not reducible and it is very unlikely that the cell could separate PNA from ETA-ΔGlu553-ΩCys612 by any natural inherent reductive activity of the cell.

Briefly, ETA-ΩCys612 is reacted with excess BMH to form non-reducible thioether bonds. The resulting product was desalted to remove unreacted BMH, mixed with the PNA and allowed to react. The reaction mixture was then loaded on a Mono Q anion exchange column and eluted with a NaCl gradient. The fractions were analyzed by 10% native polyacrylamide gel electrophoresis (PAGE) to identify the ETA-ΩCys612-PNA conjugate. The results from the gel indicated that the first peak from the Mono Q column was the conjugate whereas the second peak was unreacted ETA. This order of elution is consistent with the fact that the PNA has a free amino group at the N-terminus that is protonated at neutral pH so that the conjugate containing the PNA is eluted from the column before unreacted ETA. The fractions containing the conjugate were pooled and concentrated for subsequent analysis.

An alternative method for attaching an agent bearing a sulfhydryl group to ETA, even if the ETA does not contain a free sulfhydryl itself, is to react the ETA with succinimidyl-4-(N-maleimidomethyl)cyclohezane-1-carboxylate (SMCC). This reaction, well known to those of skill in the art, introduces maleimidyl groups at locations of primary amines in proteins. The maleimidyl groups are then available to react with agents containing a free sulfhydryl, much as the reaction with BMH described above.

Yet another strategy would be to couple ETA to an agent via available primary amines on both ETA and the agent to be coupled. This strategy makes use of the coupling agent disuccinimidyl suberate (DSS). The conjugated products of this strategy would be ETA covalently linked to the agent by a bridge between primary amino groups.

It will be recognized by those skilled in the art that there are many different schemes and strategies using various cross-linking agents that could be used to effect the conjugation of ETA and ETA derivatives to therapeutic agents for delivery to the cytoplasm.

8. Protein Purification

The present invention will employ protein purification techniques in order (i) to purify ETA for use according to of the present invention and (ii) to purify other proteins produced in vitro. Protein purification techniques are well known to those of skill in the art. These techniques tend to involve the fractionation of the cellular milieu to separated the polypeptide form other components of the mixture. Having separated target protein from the other components, the sample may be further purified using chromatographic and electrophoretic techniques to achieve complete purification. Analytical methods particularly suited to the preparation of a pure peptide are ion-exchange chromatography, exclusion chromatography; polyacrylamide gel electrophoresis; isolectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state, i.e., in this case, relative to its purity within a hepatocyte or β-cell extract. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al.,, Biochem. Biophys. Res. Comm., 76:425, 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

The basic principle of ion-exchange chromatography is that the affinity of a substance for the exchanger depends on both the electrical properties of the material and the relative affinity of other charged substances in the solvent. Hence, bound material can be eluted by changing the pH, thus altering the charge of the material, or by adding competing materials, of which salts are but one example. Because different substances have different electrical properties, the conditions for release vary with each bound molecular species. In general, to get good separation, the methods of choice are either continuous ionic strength gradient elution or stepwise elution. (A gradient of pH alone is not often used because it is difficult to set up a pH gradient without simultaneously increasing ionic strength.) For an anion exchanger, either pH and ionic strength are gradually increased or ionic strength alone is increased. For a cation exchanger, both pH and ionic strength are increased. The actual choice of the elution procedure is usually a result of trial and error and of considerations of stability. For example, for unstable materials, it is best to maintain fairly constant pH.

An ion exchanger is a solid that has chemically bound charged groups to which ions are electrostatically bound; it can exchange these ions for ions in aqueous solution. Ion exchangers can be used in column chromatography to separate molecules according to charge,; actually other features of the molecule are usually important so that the chromatographic behavior is sensitive to the charge density, charge distribution, and the size of the molecule.

The principle of ion-exchange chromatography is that charged molecules adsorb to ion exchangers reversibly so that molecules can be bound or eluted by changing the ionic environment. Separation on ion exchangers is usually accomplished in two stages: first, the substances to be separated are bound to the exchanger, using conditions that give stable and tight binding; then the column is eluted with buffers of different pH, ionic strength, or composition and the components of the buffer compete with the bound material for the binding sites.

An ion exchanger is usually a three-dimensional network or matrix that contains covalently linked charged groups. If a group is negatively charged, it will exchange positive ions and is a cation exchanger. A typical group used in cation exchangers is the sulfonic group, $SO_3^-$. If an $H^+$ is bound to the group, the exchanger is said to be in the acid form; it can, for example, exchange on $H^+$ for one $Na^+$ or two $H^+$ for one $Ca^{2+}$. The sulfonic acid group is called a strongly acidic cation exchanger. Other commonly used groups are phenolic hydroxyl and carboxyl, both weakly acidic cation exchangers. If the charged group is positive—for example, a quaternary amino group—it is a strongly basic anion exchanger. The most common weakly basic anion exchangers are aromatic or aliphatic amino groups.

The matrix can be made of various material. Commonly used materials are dextran, cellulose, agarose and copolymers of styrene and vinylbenzene in which the divinylbenzene both cross-links the polystyrene strands and contains the charged groups. Table 4 gives the composition of many ion exchangers.

The total capacity of an ion exchanger measures its ability to take up exchangeable groups per milligram of dry weight. This number is supplied by the manufacturer and is important because, if the capacity is exceeded, ions will pass through the column without binding.

TABLE 4

TABLE 4

| Matrix | Exchanger | Functional Group | Tradename |
|---|---|---|---|
| Dextran | Strong Cationic | Sulfopropyl | SP-Sephadex |
|  | Weak Cationic | Carboxymethyl | CM-Sephadex |
|  | Strong Anionic | Diethyl-(2-hydroxypropyl)-aminoethyl | QAE-Sephadex |
|  | Weak Anionic | Diethylaminoethyl | DEAE-Sephadex |
| Cellulose | Cationic | Carboxymethyl | CM-Cellulose |
|  | Cationic | Phospho | P-cel |
|  | Anionic | Diethylaminoethyl | DEAE-cellulose |
|  | Anionic | Polyethylenimine | PEI-Cellulose |
|  | Anionic | Benzoylated-naphthoylated, deiethylaminoethyl | DEAE(BND)-cellulose |
|  | Anionic | p-Aminobenzyl | PAB-cellulose |
| Styrene-divinyl-benzene | Strong Cationic | Sulfonic acid | AG 50 |
|  | Strong Anionic |  | AG 1 |
|  | Strong Cationic + | Sulfonic acid + Tetramethylammoni | AG 501 |

TABLE 4-continued

| Matrix | Exchanger | Functional Group | Tradename |
|---|---|---|---|
|  | Strong Anionic | un |  |
| Acrylic | Weak Cationic | Carboxylic | Bio-Rex 70 |
| Phenolic | Strong Cationic | Sulfonic acid | Bio-Rex 40 |
| Expoxyamine | Weak Anionic | Tertiary amino | AG-3 |

The available capacity is the capacity under particular experimental conditions (i.e., pH, ionic strength). For example, the extent to which an ion exchanger is charged depends on the pH (the effect of pH is smaller with strong ion exchangers). Another factor is ionic strength because small ions near the charged groups compete with the sample molecule for these groups. This competition is quite effective if the sample is a macromolecule because the higher diffusion coefficient of the small ion means a greater number of encounters. Clearly, as buffer concentration increases, competition becomes keener.

The porosity of the matrix is an important feature because the charged groups are both inside and outside the matrix and because the matrix also acts as a molecular sieve. Large molecules may be unable to penetrate the pores; so the capacity will decease with increasing molecular dimensions. The porosity of the polystyrene-based resins is determined by the amount of cross-linking by the divinylbenzene (porosity decreases with increasing amounts of divinylbenzene). With the Dowex and AG series, the percentage of divinylbenzene is indicated by a number after an X—hence, Dowex 50-X8 is 8% divinylbenzene Ion exchangers come in a variety of particle sizes, called mesh size. Finer mesh means an increased surface-to-volume ration and therefore increased capacity and decreased time for exchange to occur for a given volume of the exchanger. On the other hand, fine mesh means a slow flow rate, which can increase diffusional spreading. The use of very fine particles, approximately 10 $\mu$m in diameter and high pressure to maintain an adequate flow is called high-performance or high-pressure liquid chromatography or simply HPLC.

Such a collection of exchangers having such different properties—charge, capacity, porosity, mesh—makes the selection of the appropriate one for accomplishing a particular separation difficult. How to decide on the type of column material and the conditions for binding and elution is described in the following Examples.

There are a number of choice to be made when employing ion exchange chromatography as a technique. The first choice to be made is whether the exchanger is to be anionic or cationic. If the materials to be bound to the column have a single charge (i.e., either plus or minus), the choice is clear. However, many substances (e.g., proteins, viruses), carry both negative and positive charges and the net charge depends on the pH. In such cases, the primary factor is the stability of the substance at various pH values. Most proteins have a pH range of stability (i.e., in which they do not denature) in which they are either positively or negatively charged. Hence, if a protein is stable at pH values above the isoelectric point, an anion exchanger should be used; if stable at values below the isoelectric point, a cation exchanger is required.

The choice between strong and weak exchangers is also based on the effect of pH on charge and stability. For example, if a weakly ionized substance that requires very low or high pH for ionization is chromatographed, a strong ion exchanger is called for because it functions over the entire pH range. However, if the substance is labile, weak ion exchangers are preferable because strong exchangers are often capable of distorting a molecule so much that the molecule denatures. The pH at which the substance is stable must, of course, be matched to the narrow range of pH in which a particular weak exchanger is charged. Weak ion exchangers are also excellent for the separation of molecules with a high charge from those with a small charge, because the weakly charged ions usually fail to bind. Weak exchangers also show greater resolution of substances if charge differences are very small. If a macromolecule has a very strong charge, it may be impossible to elute from a strong exchanger and a weak exchanger again may be preferable. In general, weak exchangers are more useful than strong exchangers.

The Sephadex and Bio-gel exchangers offer a particular advantage for macromolecules that are unstable in low ionic strength. Because the cross-links in these materials maintain the insolubility of the matrix even if the matrix is highly polar, the density of ionizable groups can be made several times greater than is possible with cellulose ion exchangers. The increased charge density means increased affinity so that adsorption can be carried out at higher ionic strengths. On the other hand, these exchangers retain some of their molecular sieving properties so that sometimes molecular weight differences annul the distribution caused by the charge differences; the molecular sieving effect may also enhance the separation.

Small molecules are best separated on matrices with small pore size (high degree of cross-linking) because the available capacity is large, whereas macromolecules need large pore size. However, except for the Sephadex type, most ion exchangers do not afford the opportunity for matching the porosity with the molecular weight.

The cellulose ion exchangers have proved to be the best for purifying large molecules such as proteins and polynucleotides. This is because the matrix is fibrous, and hence all functional groups are on the surface and available to even the largest molecules. In may cases however, beaded forms such as DEAE-Sephacel and DEAE-Biogel P are more useful because there is a better flow rate and the molecular sieving effect aids in separation.

Selecting a mesh size is always difficult. Small mesh size improves resolution but decreases flow rate, which increases zone spreading and decreases resolution. Hence, the appropriate mesh size is usually determined empirically.

Because buffers themselves consist of ions, they can also exchange, and the pH equilibrium can be affected. To avoid these problems, the rule of buffers is adopted: use cationic buffers with anion exchangers and anionic buffers with cation exchangers. Because ionic strength is a factor in binding, a buffer should be chosen that has a high buffering capacity so that its ionic strength need not be too high. Furthermore, for best resolution, it has been generally found that the ionic conditions used to apply the sample to the column (the so-called starting conditions) should be near those used for eluting the column.

9. Pharmaceutical Compositions and Routes of Administration

The conjugates of the present invention may be employed as pharmaceutical compositions. Such compositions may be used systemically or may be administered to a particular site. For example if the conjugate will have an effect only on a specific group of cells intended for targeting, it may be administered systemically. Alternatively, certain compositions of the present invention may affect cells indiscriminately. In such a scenario, it is contemplated that the compositions would be administered at a site local to the cells intended for targeting, thereby reducing any deleterious effects to cells that are not meant to receive, and be affected by, the conjugate.

Aqueous compositions of the present invention will have an effective amount of an agent-ETA conjugate, as described elsewhere in the specification. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

The active compounds of the present invention will often be formulated for parenteral administration, e.g., formulated for injection via the intravenous, intramuscular, subcutaneous, or even intraperitoneal routes. The preparation of an aqueous composition that contains ETA conjugated with a therapeutic agent will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

10. Kits

All the essential materials and reagents required for the delivery of a therapeutic agent into the cytoplasm of a cell may be assembled together in a kit. When the components of the kit are provided in one or more liquid solutions, the liquid solution preferably is an aqueous solution, with a sterile aqueous solution being particularly preferred.

For in vivo use, the therapeutic compounds of the present invention may be formulated into a single or separate pharmaceutically acceptable syringeable composition. In this case, the container means may itself be an inhalant, syringe, pipette, eye dropper, or other such like apparatus, from which the formulation may be applied to an infected area of the body, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle.

11. Examples

The following example is included to demonstrate a preferred embodiment of the invention. It should be appreciated by those of skill in the art that the techniques disclosed in the example which follows represent techniques discovered by the inventor to function well in the practice of the invention, and thus can be considered to constitute a preferred mode for its practice. However, those of skill in the art should, in light of the present disclosure, appreciate that many changes can be made in the specific embodiment disclosed and still obtain a like or similar result without departing from the spirit and scope of the invention.

EXAMPLE 1

Transport of a Protein Nucleic Acid to the Cytoplasm

Figure 4A:
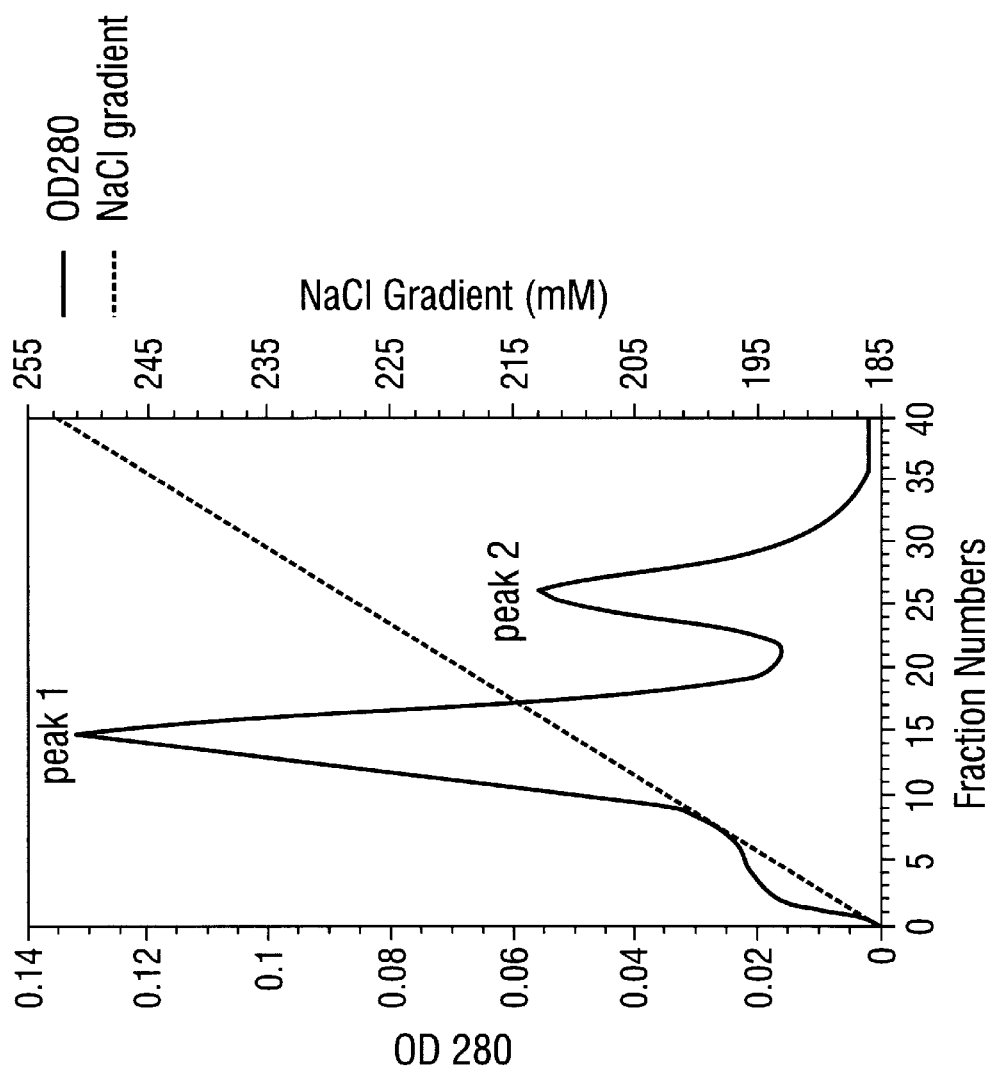
FIG. 4A and FIG. 4B.
Figure 4B:
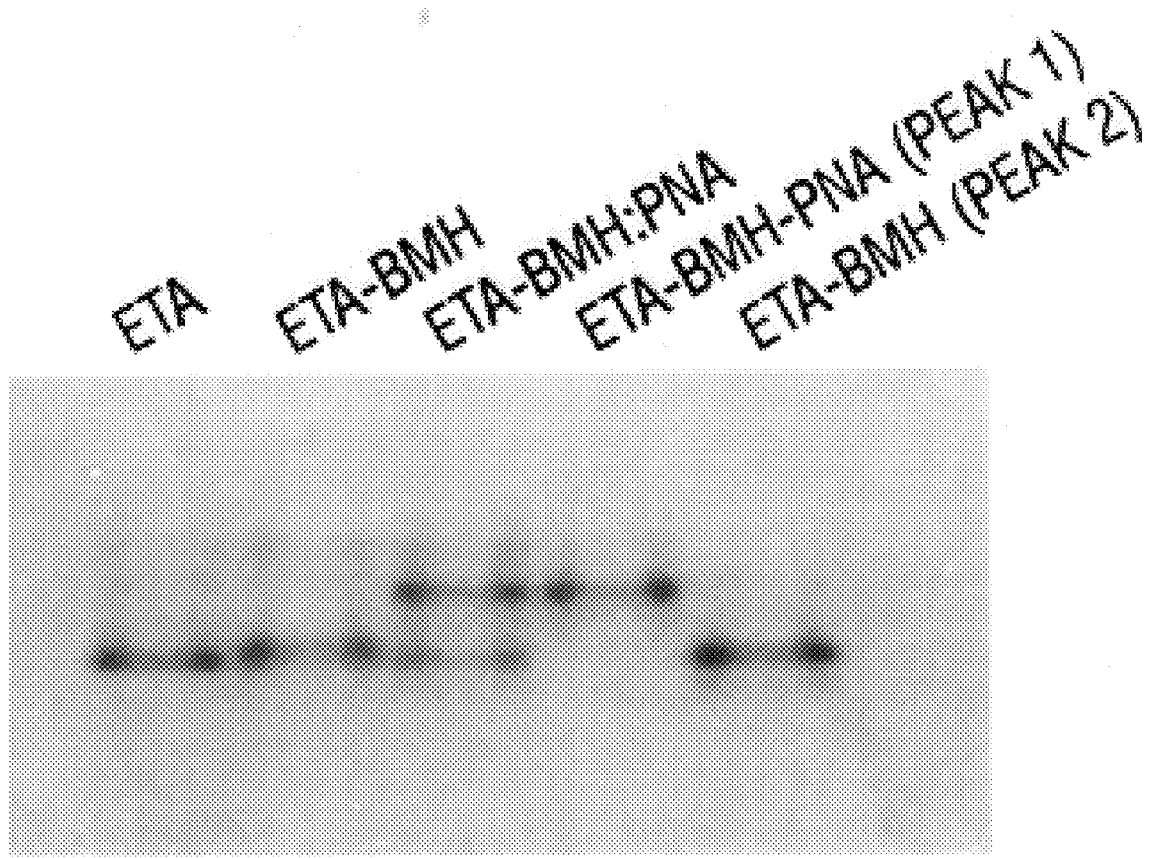

A PNA with the following sequence and base composition was prepared: CATTTTGATTACTGT-Cys (SEQ ID NO:13). Note that the PNA also contains a cysteine residue at the end to provide a free sulfhydryl for purposes of attachment to a form of ETA. The form of ETA used in this embodiment was ETA-ΩCys612, without the deletion of glutamate residue 553, so that the enzymatic activity of the ETA was maintained. However, in certain embodiments, it will be possible or even necessary to debilitate the enzymatic activity by deleting glutamate 553 as described herein above. The strategy was to attach the PNA to ETA-ΩCys612 via non-reducible thioether linkages, purify the conjugate, and determine whether the 37 kDa N-terminal component of ETA could still reach the cytoplasm and inhibit protein synthesis. If so, it would indicate that the attached PNA did not block the ability of ETA to pass through a membrane, inferring that the PNA also was carried through the membrane with the ETA.

The method for attaching ETA-ΩCys612 to the PNA, is outlined in FIG. 3. Anion exchange chromatography was used to purify ETA-ΩCys612-PNA from unreacted PNA and ETA-ΩCys612. FIG. 4A shows the results of the purification. Two major peaks absorbing at 280 nm were eluted from the column with a linear salt gradient (FIG. 4A). Analysis of the material obtained from the purification by electrophoresis in a non-denaturing polyacrylamide gel is in FIG. 4B. Lane 1 is a control showing the starting material, ETA-ΩCys612. Lane 2 is ETA-ΩCys612 after reaction with BMH. Lane 3 is material after reaction of ETA-ΩCys612-BMH with the PNA and shows that a new band, corresponding to ETA-ΩCys612-BMH-PNA, has appeared. Lane 4 is material from fractions 10–15 in FIG. 4A and demonstrates that these fractions contain ETA-ΩCys612-BMH-PNA. Lane 5 is material from fractions 25–30 in FIG. 4A, demonstrating that material in these fractions is unreacted ETA-ΩCys612. As a further precaution to ensure that ETA-ΩCys612-BMH-PNA was pure, this material was re-purified by anion exchange chromatography to provide a two-times purified sample.

Figure 5:
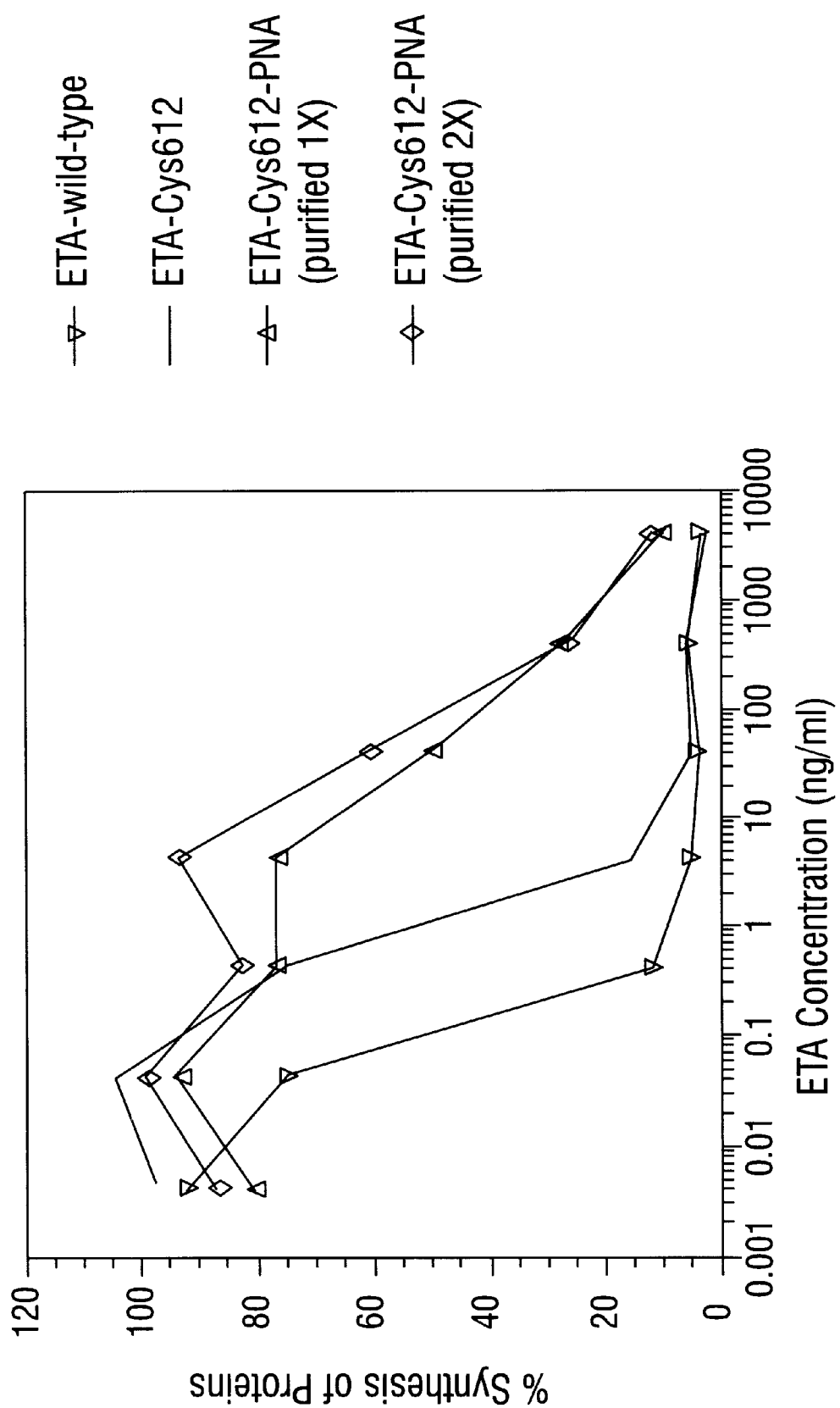
FIG. 5. Cytotoxicity assay of the non-reducible ETA-ΩCys612-PNA conjugate. Serial dilutions of the conjugate were incubated with LMTK cells for 24 h and protein synthesis was then determined by measuring $^{35}$-Met incorporation. The dose-response curves of four ETA derivatives are shown.

To evaluate the ability of ETA-ΩCys612-PNA to penetrate a membrane and reach the cytoplasm, the inventor incubated serial dilutions of the conjugate with mouse LMTK$^-$ cells which are extremely sensitive to ETA (FitzGerald et al., 1980) and measured protein synthesis by monitoring $^{35}$S-met incorporation into proteins. The results revealed that the ETA-ΩCys612-PNA conjugate was 45 times less toxic than ETA-ΩCys612 (FIG. 5). To ensure that the cytotoxic activity was not the result of a small amount of unconjugated ETA contaminating ETA-ΩCys612-PNA, the material was rechromatographed on the ion exchange column and tested again for cytotoxicity. If there had been contaminating ETA that was contributing to the inhibition of protein synthesis, then the activity should have decreased after the second purification, but it did not (FIG. 6, ETA-ΩCys612-PNA, purified 2x). Although not as active as intact ETA, the ETA-ΩCys612-PNA still reduced protein synthesis effectively at low concentrations, suggesting that it entered the cytoplasm despite the presence of the attached PNA. This is evidence that ETA can carry a PNA across a membrane and into the cytoplasm.

A summary of the effect of ETA-ΩCys612-BMH-PNA on protein synthesis from multiple experiments is shown in Table 5 below. Row 1 is a control to show the effect of native ETA on protein synthesis. Row 2 shows the effect of ETA-ΩCys612 on protein synthesis and demonstrates that ETA-ΩCys612 is a potent inhibitor of protein synthesis. Row 3 shows the effect of one-time purified ETA-ΩCys612-BMH-PNA and row 4 is two-times purified ETA-ΩCys612-BMH-PNA. It is apparent that attaching a PNA to ETA-ΩCys612 increases the concentration required to inhibit protein synthesis by about 45-fold compared to ETA-ΩCys612. This is a remarkably small increase in the IC$_{50}$ considering that the toxin must now drag a PNA with it when it crosses a membrane. Note also that there was no change in the IC$_{50}$ when two-times purified material was used. This indicates that the activity of the ETA-ΩCys612-BMH-PNA from the first purification cannot be due to a small amount of contaminating unconjugated ETA; if it were, the amount of ETA-ΩCys612-BMH-PNA required to inhibit protein synthesis should have gone up as contaminants were incrementally removed. Altogether this data teaches that attaching a PNA to ETA-ΩCys612 slightly reduces the efficiency at which the toxin can cross a membrane, but that it nevertheless does cross and presumably carries with it the PNA.

TABLE 5

The effect of ETA-ΩCys612-BMH-PNA on protein synthesis

| MATERIAL | IC$_{50}$ (ng/ml ± S.D.)[1] |
|---|---|
| ETA | .09 ± 0.03 (n = 3) |
| ETA-ΩCys612 | 1.1 ± 0.4 (n = 4) |
| ETA-ΩCys612-BMH-PNA (purified 1x) | 45 ± 14 (n = 2) |
| ETA-ΩCys612-BMH-PNA (purified 2x) | 45 ± 10 (n = 3) |

[1]The IC$_{50}$ is the concentration required to reduce protein synthesis in mouse cells by 50%. n is the number of independent determinations of the IC$_{50}$. The standard deviation of the determinations is shown.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Allured et al., "Structure of exotoxin A of *Pseudomonas aeruginosa* at 3.0 angstrom resolution," *Proc. Natl. Acad. Sci. USA*, 83:1320–1324, 1986.
Bau and Draper, "Ricin intoxicates End4 mutants that have an aberrant Golgi complex," *J. Biol. Chem.*, 268:19939–19942, 1993.
Bedzyk et al., "Active site structure and antigen binding properties of idiotypically cross-reactive anti-fluorescein monoclonal antibodies," *J. Biol. Chem.*, 265(1):133–138, 1990.
Bedzyk et al., "Immunological and structural characterization of a high affinity anti-fluorescein single-chain antibody," *J. Biol. Chem.*, 265(30):18615–20, 1990.
Benhar et al., "Pseudomonas exotoxin A mutants: replacement of surface-exposed residues in domain III with cysteine residues that can be modified with polyethyleme glycol in a site-specific manner," *J. Biol. Chem.*, 269:13398–13404, 1994.
Bosshart et al., "The cytoplasmic domain mediates localization of furin to the trans-Golgi network en route to the endosomal/lysosomal system," *J. Cell Biol.*, 126, 1157–1172, 1994.
Braakman et al., "Role of ATP and disulphide bonds during protein folding in the endoplasmic reticulum," *Nature* 356:260–262, 1992.
Burbage et al., *Leuk Res*, 21(7):681–690, 1997.
Campbell et al., *J. Mol. Biol.*, 180:1–19, 1984.
Capaldi et al., *Biochem. Biophys. Res. Comm.*, 76:425, 1977.
Chaudhary et al., "Pseudomonas exotoxin contains a specific sequence at the carboxyl terminus that is required for cytotoxicity," *Proc. Natl. Acad. Sci. USA*, 87:308–312, 1990.

Chaudhary et al., "A recombinant immunotoxin consisting of two antibody variable domains fused to Pseudomonas exotoxin," *Nature,* 339(6223):394–397, 1989.

Chiron et al., "Cleavage of Pseudomonas exotoxin and diphtheria toxin by a furin-like enzyme prepared from beef liver," *J. Biol. Chem.,* 269:18167–18176, 1994.

Clairmont et al., "Translocation of ATP into the lumen of rough endoplasmic reticulum-derived vesicles and its binding to luminal proteins including BiP (GRP 78) and GRP 94," *J. Biol. Chem.,* 267: 3983–3990, 1994.

Cook et al., "In vitro splicing of the ribosomal RNA precursor of Tetrahymena: involvement of a guanosine nucleotide in the excision of the intervening sequence," *Cell,* 27:487–496, 1981.

Cosson and Letourneur, "Coatomer interaction with di-lysine endoplasmic reticulum retention motifs," *Science,* 263:1629–1631, 1994.

Demidov et al., "Stability of peptide nucleic acids in human serum and cellular extracts," *Biochem. Pharmacol.,* 48:1310–1313, 1994.

Douglas and Collier, "Exotoxin A of *Pseudomonas aeruginosa*: substitution of glutamic acid 553 with aspartic acid drastically reduces toxicity and enzymatic activity," *J. Bacteriol.,* 169(11):4967–4971, 1987.

Douglas et al., "Exotoxin A of *Pseudomonas aeruginosa*: active, cloned toxin is secreted into the periplasmic space of *Escherichia coli,*" *J Bacteriol.,* 169(11):4962–4966, 1987.

Endo et al., "The mechanism of action of ricin-And related toxic lectins on eukaryotic ribosomes: the site and the characteristics of the modification in 28 S ribosomal RNA caused by the toxins," *J. Biol. Chem..* 262:5908–5912, 1987.

FitzGerald et al.,, "Receptor-mediated internalization of Pseudomonas toxin by mouse fibroblasts," *Cell,* 21(3):867–873, 1980.

Forster and Symons, "Self-cleavage of plus and minus RNAs of a virusoid and a structural model for the active sites," *Cell,* 49:211–220, 1987

Frankel and Pabo, "Cellular uptake of the tat protein from human immunodeficiency virus," *Cell,* 55(6):1189–1193, 1988.

Gefter et al., *Somatic Cell Genet.,* 3:231–236, 1977.

Gerlach et al., "Construction of a plant disease resistance gene from the satellite RNA of tobacco rinspot virus," *Nature (London),* 328:802–805, 1987.

Goding, *In: Monoclonal Antibodies: Principles and Practice,* 2d ed., Academic Press, Orlando, Fla., pp. 60–61, and 71–74, 1986.

Gordon and Leppla, "Proteolytic activation of bacterial toxins: role of bacterial and host cell proteases," *Infect. Immun.,* 62:333–340, 1994.

Gordon et al., "Proteolytic activation of bacterial toxins by eukaryotic cells is performed by furin and by additional cellular proteases," *Infect. Immun.,* 63:82–87, 1995.

Gossen and Bujard, "Tight control of gene expression in mammalian cells by tetracycline-responsive promoters," *Proc. Natl. Acad. Sci. USA,* 89:5547–5551, 1002.

Gribskov and Burgess, *Nucl. Acids Res.,* 14:6745, 1986, as described by Schwartz and Dayhoff, eds., Atlas of Protein Sequence and Structure, National Biomedical Research Foundation, pp. 353–358, 1979

Guo et al., "Disruptions in Golgi structure and membrane traffic in a conditional lethal mammalian cell mutant are corrected by __-COP." *J. Cell Biol.,* 125:1213–1224, 1994.

Hanvey et al., "Antisense properties of peptide nucleic acids," *Science,* 258:1481–1485, 1992.

Harlow and Lane, *In: Antibodies: A Laboratory Manual,* Cold Spring Harbor Laboratory, Cold Spring Harbor, N.Y., 1988.

Hobbie et al., "Isolation of three classes of conditional lethal Chinese hamster ovary cell mutants with temperature-dependent defects in low density lipoprotein receptor stability and intracellular membrane transport," *J. Biol. Chem.,* 269:20958–20970, 1994.

Hollstein et al., *Science,* 253:49–53, 1991.

Hudson and Grillo, "Brefeldin A enhancement of ricin-A-chain immunotoxins and blockade of intact ricin, modeccin and abrin," *J. Biol. Chem.,* 266:18586–18592, 1991.

Iglewski and Sadoff, "Toxin inhibitors of protein synthesis: production, purification, and assay of *Pseudomonas aeruginosa* toxin A," *Methods Enzymol.,* 60:780–793, 1979.

Inocencio et al., "Furin activates Pseudomonas exotoxin A by specific cleavage in vivo and in vitro," *J. Biol. Chem.,* 269:31831–31835, 1994.

Joyce, "RNA evolution and the origins of life," *Nature,* 338:217–244, 1989.

Kao and Draper, "Retention of secretory proteins in an intermediate compartment and disappearance of the Golgi complex in an END4 mutant of Chinese hamster ovary cells," *J. Cell Biol.,* 117:701–715, 1992.

Kartenbeck et al., "Endocytosis of simian virus 40 into the endoplasmic reticulum," *J. Cell Biol.,* 109:2721–2729, 1989.

Kim and Cook, "Three dimensional model of the active site of the self-splicing rRNA precursor or Tetrahymena," *Proc. Natl. Acad. Sci. USA,* 84:8788–8792, 1987.

Kitamoto et al., "Enterokinase, the initiator of intestinal digestion, is a mosaic protease composed of a distinctive assortment of domains," *Proc. Natl. Acad. Sci. USA,* 91:7588–7592, 1984.

Kohler and Milstein, *Eur. J. Immunol.,* 6:511–519, 1976.

Kohler and Milstein, *Nature,* 256:495–497, 1975.

Kounnas et al., "The 2-macroglobulin receptor/low density lipoprotein receptor-related protein binds and internalizes Pseudomonas exotoxin A," *J. Biol. Chem.,* 267:12420–12423, 1992.

Kyte and Doolittle, "A simple method for displaying the hydropathic character of a protein," *J. Mol. Biol.,* 157(1):105–132, 1982.

Leduc et al., "Activation of human furin precursor processing endoprotease occurs by an intramolecular autoproteolyic cleavage," *J. Biol. Chem.,* 267:14304–14308, 1992.

Lemaitre et al., "Specific antiviral activity of a poly(L-lysine)-conjugated oligodeoxyribonucleotide sequence complementary to vesicular stomatitus virus N protein mRNA initiation site," *Proc. Natl. Acad. Sci. USA,* 84:648–652, 1987.

Leonetti et al., "Antibody-targeted liposomes containing oligodeoxyribonucleotides complementary to viral RNA selectively inhibit viral replication," *Proc. Natl. Acad. Sci. USA,* 87:2448–2451, 1990.

Letourneur et al., "Coatomer is essential for retrieval of dilysine-tagged proteins to the endoplasmic reticulum," *Cell,* 79:1199–1207, 1994.

Lidor et al., *Am. J. Obstet. Gynecol.,* 177(3):579–585, 1997.

Lin and Guidotti, "Cloning and expression of a cDNA coding for a rat liver plasma membrane ecto-ATPase: the primary structure of the ecto-ATPase is similar to that of human biliary glycoprotein," *J. Biol. Chem.,* 264:14408–14414, 1989.

Lukac and Collier, *J. Biol. Chem.* 263:6146–6149, 1988.

Lukac et al., "Toxoid of *Pseudomonas aeruginosa* exotoxin A generated by deletion of an active-site residue," *Infect. Immun.,* 53:3095–3098, 1988.

Madshus and Collier, "Effects of eliminating a disulfide bridge within domain II of *Pseudomonas aeruginosa* exotoxin A," *Infect. Immun.,* 57:1873–1878, 1989.

Mann and Frankel, "Endocytosis and targeting of exogenous HIV-1 Tat protein," *EMBO J.,* 10(7):1733–1739, 1991.

Massuda et al., *Proc. Natl. Acad. Sci. USA,* 94(26):14701–14706, 1997.

Melton et al., "Efficient in vitro synthesis of biologically active RNA and RNA hybridization probes from plasmids containing a bacteriophage SP6 promotor," *Nucl. Acids Res.,* 18:7035–7056, 1984.

Michel and Westhof, "Modeling of the three-dimensional architecture of group I catalytic introns based on comparative sequence analysis," *J. Mol. Biol.,* 216:585–610, 1990.

Miesenack and Rothman, "The capacity to retrieve escaped ER proteins extends to the trans-most cisterna of the Golgi stack," *J. Cell Biol.,* 129:309–319, 1995.

Moehring et al., "Expression of mouse furin in a Chinese hamster cell resistant to Pseudomonas exotoxin A and viruses complements the genetic lesion," *J. Biol. Chem.,* 268:2590–2594, 1993.

Nakano et al., "A temperature-sensitive Chinese hamster ovary cell mutant pleiotropically defective in protein export," *Biochim. Biophys. Acta,* 845:324–332, 1985.

Nielsen et al., "Sequence-selective recognition of DNA by strand displacement with a thymine-substituted polyamide," *Science,* 254:1497–1500, 1991.

Odin and Obrink, "Quantitative determination of the organ distribution of the cell adhesion molecule cell-CAM 105 by radioimmunoassay," *Exp. Cell Res.,* 171:1–15, 1987.

Ogata et al., "Processing of Pseudomonas exotoxin by a cellular protease results in the generation of a 37,000-Da toxin fragment that is translocated to the cytosol," *J. Biol. Chem.,* 265:20678–20685, 1990.

Ogata et al., "Cell-mediated cleavage of Pseudomonas exotoxin between $Arg^{279}$ and $Gly^{280}$ generates the enzymatically active fragment which translocates to the cytosol," *J. Biol. Chem.,* 267:25396–25401, 1992.

Olsnes and Pihl, "Toxic lectins and related proteins," *In: Molecular Action of Toxins and Viruses,* P. Cohen, and S. van Heyningen, eds. (Amsterdam: Elsevier/North Holland), pp. 51–105, 1982.

Olsnes and Sandvig, "Entry of polypeptide toxins into animal cells," *In: Endocytosis,* I. Pastan and M. C. Willingham, eds., Penum Publishing Corporation, New York, pp. 195–234, 1985.

Pastan and FitzGerald, "Recombinant toxins for cancer treatment," *Science,* 254:1173–1177, 1991.

Pastan et al., "Recombinant toxins as novel therapeutic agents," *Ann. Rev. Biochem.,* 61:331–354, 1992.

Pelham et al., "Toxin entry: how reversible is the secretory pathway?," *Trends Cell Biol.,* 2:183–185, 1992.

Prior et al., "Barnase toxin: a new chimeric toxin composed of Pseudomonas exotoxin A and barnase," *Cell,* 64:1017–1023, 1991.

Prior et al., "Translocation mediated by domain II of Pseudomonas exotoxin A: transport of barnase into the cytosol," *Biochem.,* 31:3555–3559, 1992.

Ramakrishnan et al., "Recombinant ricin-A chain conjugated to monoclonal antibodies: improved tumor cell inhibition in the presence of lysosomotropic compounds," *Cancer Res.,* 49:613–617, 1989.

Reinhold-Hurek and Shub, "Self-splicing introns in the tRNA genes of widely divergent bacteria," *Nature,* 357:173–176, 1992.

Remington's Pharmaceutical Sciences, 15th ed., pp. 1035–1038 and 1570–1580.

Sambrook et al., *In: Molecular cloning: A laboratory manual,* Cold Spring Harbor Laboratory, Cold Spring Harbor, N.Y., 1989.

Sandvig et al., "Retrograde transport of endocytosed Shiga toxin to the endoplasmic reticulum," *Nature,* 358:510–512, 1992.

Sandvig et al., "Retrograde transport from the Golgi complex to the ER of both shiga toxin and the nontoxic shiga B-fragment is regulated by butyric acid and cAMP," *J. Cell Biol.,* 126:53–64, 1994.

Sarver et al., "Ribozymes as potential anti-HIV-1 therapeutic agents," *Science,* 247:1222–1225, 1990.

Scanlon et al., "Ribozyme-mediated cleavages of c-fos mRNA reduce gene expression of DNA synthesis enzymes and metallothionein," *Proc. Nat'l. Acad. Sci. USA,* 88:10591–10595, 1991.

Scatchard, "The attraction of proteins for small molecules and ions," *Ann. N.Y. Acad. Sci.,* 51:660–672, 1949.

Serrano et al., *Nature,* 366:704–707, 1993.

Serrano et al., *Science,* 267:249–252, 1995.

Siegall et al., "Functional analysis of domains II, Ib and III of Pseudomonas exotoxin," *J. Biol. Chem.,* 264:14256–14261, 1989.

Tatu et al., "Membrane glycoprotein folding, oligomerization and intracellular transport: effects of dithiothreitol in living cells," *EMBO J.,* 12:2151–2157, 1993.

U.S. Pat. No. 4,196,265

U.S. Pat. No. 4,554,101

U.S. Pat. No. 5,354,855

U.S. Pat. No. 5,359,046

Vestweber and Schatz, "DNA-protein conjugates can enter mitochondria via the import pathway," *Nature,* 338:170–172, 1989.

Wales et al., "Addition of an ER retention signal to the ricin-A chain increases the cytotoxicity of the holotoxin," *Exp. Cell Res.,* 203:1–4, 1992.

Wang et al., "Impaired secretion and fluid-phase endocytosis in the End4 mutant of Chinese hamster ovary cells," *J. Biol. Chem.,* 265:20179–20187, 1990.

Weinberg et al., Positive and negative controls on cell growth. *Biochemistry,* 28:8263–8269, 1989.

Wittung et al., "Phospholipid membrane permeability of peptide nucleic acid," *FEBS Letters,* 365:27–29, 1995.

Zhao and London, "Conformation and model membrane interactions of diphtheria toxin fragment A," *J. Biol. Chem.,* 263(30):15369–15377, 1988.

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
       (A) LENGTH: 2760 base pairs
       (B) TYPE: nucleic acid
       (C) STRANDEDNESS: single
       (D) TOPOLOGY: linear (xi) SEQUENCE DESCRIPTION: SEQ ID NO:1:

```
CTGCAGCTGG TCAGGCCGTT TCCGCAACGC TTGAAGTCCT GGCCGATATA CCGGCAGGGC      60

CAGCCATCGT TCGACGAATA AAGCCACCTC AGCCATGATG CCCTTTCCAT CCCCAGCGGA     120

ACCCCGACAT GGACGCCAAA GCCCTGCTCC TCGGCAGCCT CTGCCTGGCC GCCCCATTCG     180

CCGACGCGGC GACGCTCGAC AATGCTCTCT CCGCCTGCCT CGCCGCCCGG CTCGGTGCAC     240

CGCACACGGC GGAGGGCCAG TTGCACCTGC CACTCACCCT TGAGGCCCGG CGCTCCACCG     300

GCGAATGCGG CTGTACCTCG GCGCTGGTGC GATATCGGCT GCTGGCCAGG GGCGCCAGCG     360

CCGACAGCCT CGTGCTTCAA GAGGGCTGCT CGATAGTCGC CAGGACACGC CGCGCACGCT     420

GACCCTGGCG GCGGACGCCG GCTTGGCGAG CGGCCGCGAA CTGGTCGTCA CCCTGGGTTG     480

TCAGGCGCCT GACTGACAGG CCGGGCTGCC ACCACCAGGC CGAGATGGAC GCCCTGCATG     540

TATCCTCCGA TCGGCAAGCC TCCCGTTCGC ACATTCACCA CTCTGCAATC CAGTTCATAA     600

ATCCCATAAA AGCCCTCTTC CGCTCCCCGC CAGCCTCCCC GCATCCCGCA CCCTAGACGC     660

CCCGCCGCTC TCCGCCGGCT CGCCCGACAA GAAAAACCAA CCGCTCGATC AGCCTCATCC     720

TTCACCCATC ACAGGAGCCA TCGCGATGCA CCTGATACCC CATTGGATCC CCCTGGTCGC     780

CAGCCTCGGC CTGCTCGCCG GCGGCTCGTC CGCGTCCGCC GCCGAGGAAG CCTTCGACCT     840

CTGGAACGAA TGCGCCAAAG CCTGCGTGCT CGACCTCAAG GACGGCGTGC GTTCCAGCCG     900

CATGAGCGTC GACCCGGCCA TCGCCGACAC CAACGGCCAG GGCGTGCTGC ACTACTCCAT     960

GGTCCTGGAG GGCGGCAACG ACGCGCTCAA GCTGGCCATC GACAACGCCC TCAGCATCAC    1020

CAGCGACGGC CTGACCATCC GCCTCGAAGG CGGCGTCGAG CCGAACAAGC CGGTGCGCTA    1080

CAGCTACACG CGCCAGGCGC GCGGCAGTTG GTCGCTGAAC TGGCTGGTAC CGATCGGCCA    1140

CGAGAAGCCC TCGAACATCA AGGTGTTCAT CCACGAACTG AACGCCGGCA ACCAGCTCAG    1200

CCACATGTCG CCGATCTACA CCATCGAGAT GGGCGACGAG TTGCTGGCGA AGCTGGCGCG    1260

CGATGCCACC TTCTTCGTCA GGGCGCACGA GAGCAACGAG ATGCAGCCGA CGCTCGCCAT    1320

CAGCCATGCC GGGGTCAGCG TGGTCATGGC CCAGACCCAG CCGCGCCGGG AAAAGCGCTG    1380

GAGCGAATGG GCCAGCGGCA AGGTGTTGTG CCTGCTCGAC CCGCTGGACG GGTCTACAA     1440

CTACCTCGCC CAGCAACGCT GCAACCTCGA CGATACCTGG GAAGGCAAGA TCTACCGGGT    1500

GCTCGCCGGC AACCCGGCGA AGCATGACCT GGACATCAAA CCCACGGTCA TCAGTCATCG    1560

CCTGCACTTT CCCGAGGGCG GCAGCCTGGC CGCGCTGACC GCGCACCAGG CTTGCCACCT    1620

GCCGCTGGAG ACTTTCACCC GTCATCGCCA GCCGCGCGGC TGGGAACAAC TGGAGCAGTG    1680

CGGCTATCCG GTGCAGCGGC TGGTCGCCCT CTACCTGGCG GCGCGGCTGT CGTGGAACCA    1740

GGTCGACCAG GTGATCCGCA ACGCCCTGGC CAGCCCCGGC AGCGGCGGCG ACCTGGGCGA    1800

AGCGATCCGC GAGCAGCCGG AGCAGGCCCG TCTGGCCCTG ACCCTGGCCG CCGCCGAGAG    1860
```

```
CGAGCGCTTC GTCCGGCAGG GCACCGGCAA CGACGAGGCC GGCGCGGCCA ACGCCGACGT    1920

GGTGAGCCTG ACCTGCCCGG TCGCCGCCGG TGAATGCGCG GGCCCGGCGG ACAGCGGCGA    1980

CGCCCTGCTG GAGCGCAACT ATCCCACTGG CGCGGAGTTC CTCGGCGACG GCGGCGACGT    2040

CAGCTTCAGC ACCCGCGGCA CGCAGAACTG GACGGTGGAG CGGCTGCTCC AGGCGCACCG    2100

CCAACTGGAG GAGCGCGGCT ATGTGTTCGT CGGCTACCAC GGCACCTTCC TCGAAGCGGC    2160

GCAAAGCATC GTCTTCGGCG GGGTGCGCGC GCGCAGCCAG GACCTCGACG CGATCTGGCG    2220

CGGTTTCTAT ATCGCCGGCG ATCCGGCGCT GGCCTACGGC TACGCCCAGG ACCAGGAACC    2280

CGACGCACGC GGCCGGATCC GCAACGGTGC CCTGCTGCGG GTCTATGTGC CGCGCTCGAG    2340

CCTGCCGGGC TTCTACCGCA CCAGCCTGAC CCTGGCCGCG CCGGAGGCGG CGGGCGAGGT    2400

CGAACGGCTG ATCGGCCATC CGCTGCCGCT GCGCCTGGAC GCCATCACCG GCCCCGAGGA    2460

GGAAGGCGGG CGCCTGGAGA CCATTCTCGG CTGGCCGCTG GCCGAGCGCA CCGTGGTGAT    2520

TCCCTCGGCG ATCCCCACCG ACCCGCGCAA CGTCGGCGGC GACCTCGACC CGTCCAGCAT    2580

CCCCGACAAG GAACAGGCGA TCAGCGCCCT GCCGGACTAC GCCAGCCAGC CCGGCAAACC    2640

GCCGCGCGAG GACCTGAAGT AACTGCCGCG ACCGGCCGGC TCCCTTCGCA GGAGCCGGCC    2700

TTCTCGGGGC CTGGCCATAC ATCAGGTTTT CCTGATGCCA GCCCAATCGA ATATGAATTC    2760
```

(2) INFORMATION FOR SEQ ID NO:2:

(i) SEQUENCE CHARACTERISTICS:
        (A) LENGTH: 638 amino acids
        (B) TYPE: amino acid
        (C) STRANDEDNESS:
        (D) TOPOLOGY: linear (xi) SEQUENCE DESCRIPTION: SEQ ID NO:2:

```
Met His Leu Ile Pro His Trp Ile Pro Leu Val Ala Ser Leu Gly Leu
1               5                   10                  15

Leu Ala Gly Gly Ser Ser Ala Ser Ala Ala Glu Glu Ala Phe Asp Leu
            20                  25                  30

Trp Asn Glu Cys Ala Lys Ala Cys Val Leu Asp Leu Lys Asp Gly Val
        35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Glu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Thr Gln Pro Arg Arg
```

-continued

```
             195                 200                 205
Glu Lys Arg Trp Ser Glu Trp Ala Ser Gly Lys Val Leu Cys Leu Leu
210                 215                 220
Asp Pro Leu Asp Gly Val Tyr Asn Tyr Leu Ala Gln Gln Arg Cys Asn
225                 230                 235                 240
Leu Asp Asp Thr Trp Glu Gly Lys Ile Tyr Arg Val Leu Ala Gly Asn
                245                 250                 255
Pro Ala Lys His Asp Leu Asp Ile Lys Pro Thr Val Ile Ser His Arg
            260                 265                 270
Leu His Phe Pro Glu Gly Gly Ser Leu Ala Ala Leu Thr Ala His Gln
        275                 280                 285
Ala Cys His Leu Pro Leu Glu Thr Phe Thr Arg His Arg Gln Pro Arg
290                 295                 300
Gly Trp Glu Gln Leu Glu Gln Cys Gly Tyr Pro Val Gln Arg Leu Val
305                 310                 315                 320
Ala Leu Tyr Leu Ala Ala Arg Leu Ser Trp Asn Gln Val Asp Gln Val
                325                 330                 335
Ile Arg Asn Ala Leu Ala Ser Pro Gly Ser Gly Gly Asp Leu Gly Glu
            340                 345                 350
Ala Ile Arg Glu Gln Pro Glu Gln Ala Arg Leu Ala Leu Thr Leu Ala
        355                 360                 365
Ala Ala Glu Ser Glu Arg Phe Val Arg Gln Gly Thr Gly Asn Asp Glu
370                 375                 380
Ala Gly Ala Ala Asn Ala Asp Val Val Ser Leu Thr Cys Pro Val Ala
385                 390                 395                 400
Ala Gly Glu Cys Ala Gly Pro Ala Asp Ser Gly Asp Ala Leu Leu Glu
                405                 410                 415
Arg Asn Tyr Pro Thr Gly Ala Glu Phe Leu Gly Asp Gly Asp Val
            420                 425                 430
Ser Phe Ser Thr Arg Gly Thr Gln Asn Trp Thr Val Glu Arg Leu Leu
        435                 440                 445
Gln Ala His Arg Gln Leu Glu Arg Gly Tyr Val Phe Val Gly Tyr
450                 455                 460
His Gly Thr Phe Leu Glu Ala Ala Gln Ser Ile Val Phe Gly Gly Val
465                 470                 475                 480
Arg Ala Arg Ser Gln Asp Leu Asp Ala Ile Trp Arg Gly Phe Tyr Ile
                485                 490                 495
Ala Gly Asp Pro Ala Leu Ala Tyr Gly Tyr Ala Gln Asp Gln Glu Pro
            500                 505                 510
Asp Ala Arg Gly Arg Ile Arg Asn Gly Ala Leu Leu Arg Val Tyr Val
        515                 520                 525
Pro Arg Ser Ser Leu Pro Gly Phe Tyr Arg Thr Ser Leu Thr Leu Ala
530                 535                 540
Ala Pro Glu Ala Ala Gly Glu Val Glu Arg Leu Ile Gly His Pro Leu
545                 550                 555                 560
Pro Leu Arg Leu Asp Ala Ile Thr Gly Pro Glu Glu Gly Gly Arg
                565                 570                 575
Leu Glu Thr Ile Leu Gly Trp Pro Leu Ala Glu Arg Thr Val Val Ile
            580                 585                 590
Pro Ser Ala Ile Pro Thr Asp Pro Arg Asn Val Gly Gly Asp Leu Asp
        595                 600                 605
Pro Ser Ser Ile Pro Asp Lys Glu Gln Ala Ile Ser Ala Leu Pro Asp
610                 615                 620
```

```
Tyr Ala Ser Gln Pro Gly Lys Pro Pro Arg Glu Asp Leu Lys
625                 630                 635

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:3:

GACTGTTACG CCAGCCAGCC CGGCAAACCA CCGCGTGAG                                  39

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:4:

Asp Cys Tyr Ala Ser Gln Pro Gly Lys Pro Pro Arg Glu
1               5                   10

(2) INFORMATION FOR SEQ ID NO:5:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:5:

Tyr Ala Ser Gln Pro Gly Lys Pro Pro Arg Glu Asp Leu Lys
1               5                   10

(2) INFORMATION FOR SEQ ID NO:6:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:6:

ACAATGCGGT CGGTCGGGCC GTTTGGTGGC GCACTCCTG                                  39

(2) INFORMATION FOR SEQ ID NO:7:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:7:

TACGCCAGCC AGCCCGGCAA ACCGCCGCGC GAGGACCTGA AG                              42

(2) INFORMATION FOR SEQ ID NO:8:

(i) SEQUENCE CHARACTERISTICS:
        (A) LENGTH: 84 base pairs
        (B) TYPE: nucleic acid
        (C) STRANDEDNESS: single
        (D) TOPOLOGY: linear
```

(xi) SEQUENCE DESCRIPTION: SEQ ID NO:8:

TACGCCAGCC AGCCCGGCAA ACCGCCGCGC GAGGACTGTT ACGCCAGCCA GCCCGGCAAA    60

CCACCGCGTG AGGACCTGAA GTAA                                          84

(2) INFORMATION FOR SEQ ID NO:9:

(i) SEQUENCE CHARACTERISTICS:
        (A) LENGTH: 27 amino acids
        (B) TYPE: amino acid
        (C) STRANDEDNESS:
        (D) TOPOLOGY: linear (xi) SEQUENCE DESCRIPTION: SEQ ID NO:9:

Tyr Ala Ser Gln Pro Gly Lys Pro Pro Arg Glu Asp Cys Tyr Ala Ser
1               5                   10                  15

Gln Pro Gly Lys Pro Pro Arg Glu Asp Leu Lys
            20                  25

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:10:

Arg Glu Asp Leu Lys
1               5

(2) INFORMATION FOR SEQ ID NO:11:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:11:

Arg Glu Asp Leu
1

(2) INFORMATION FOR SEQ ID NO:12:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:12:

Lys Asp Glu Leu
1

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:13:

CATTTTGATT ACTGT                                                    15

What is claimed is:

1. A method of providing a molecule to a cell comprising:
   (i) conjugating said molecule to a detoxified exotoxin A (ETA) in domain III of ETA, wherein said detoxified ETA also contains a deletion, insertion or substitution in domain III of ETA; and
   (ii) contacting the conjugate with said cell,
whereby said conjugate is delivered to the cytoplasm of said cell.

2. The method of claim 1, wherein said molecule is a nucleic acid, a peptide, a peptide-nucleic acid, an antibody, a single-chain antibody or a pharmaceutical.

3. The method of claim 1, wherein said conjugating is via a covalent bond.

4. The method of claim 1, wherein said conjugating is via a non-covalent bond.

5. The method of claim 1, wherein said detoxified ETA is produced recombinantly.

6. The method of claim 1, wherein said detoxified ETA contains a sulfur residue not found in the natural toxin.

7. The method of claim 1, wherein said detoxified ETA contains a deletion of the glutamate residue at position 553 of the natural toxin.

8. The method of claim 1, wherein said providing is performed in vitro or in vivo.

9. The method of claim 1, wherein said cell is a CHO cell, a CV-1 cell, a Vero cell, an embryonic stem cell, a HeLa cell, a smooth muscle cell, a fibroblast, a tumor cell, a B-lymphocyte or a T-lymphocyte.

10. The method of claim 2, wherein said molecule is a nucleic acid.

11. The method of claim 2, wherein said molecule is a peptide.

12. The method of claim 2, wherein said molecule is a peptide-nucleic acid.

13. The method of claim 2, wherein said molecule is an antibody.

14. The method of claim 2, wherein said molecule is a single chain antibody.

15. The method of claim 2, wherein said molecule is a pharmaceutical.

16. The method of claim 10, wherein said nucleic acid is DNA.

17. The method of claim 11, wherein said peptide is a polypeptide.

18. The method of claim 13, wherein said antibody or single-chain antibody has catalytic function.

19. The method of claim 16, wherein said DNA is under the control of a eukaryotic promoter.

20. The method of claim 16, wherein said DNA encodes an antisense construct.

21. The method of claim 19, wherein said DNA encodes a nucleic acid binding protein, a single-chain antibody, a tumor suppressor, a cytokine, an oncogene, a hormone or a toxin.

22. The method of claim 19, wherein said eukaryotic promoter is the CMV IE promoter, the β-actin promoter, the E1A promoter, the TET promoter or the ecdysone promoter.

23. The method of claim 20, wherein said antisense construct targets an oncogene or a viral protein.

24. The method of claim 17, wherein said polypeptide is an enzyme, an antibody or a nucleic acid binding protein.

25. The method of claim 3, wherein said bond is reducible.

26. The method of claim 25, wherein said bond is a carbon-sulfur bond, carbon-carbon bond, carbon-oxygen bond or a carbon-nitrogen bond.

27. The method of claim 14, wherein said single-chain antibody has catalytic function.

28. The method of claim 26, wherein said bond is a carbon-sulfur bond, and the sulfur residue of said carbon-sulfur bond is a component of said detoxified ETA.

29. A conjugate comprising:
   (i) a detoxified ETA, wherein said detoxified ETA contains a deletion, insertion or substitution in domain III of ETA; and
   (ii) another molecule conjugated to said detoxified ETA in domain III.

30. The conjugate of claim 29, wherein said molecule is a nucleic acid, a peptide, a peptide-nucleic acid, an antibody, a single chain antibody or a pharmaceutical.

31. The conjugate of claim 29, wherein said conjugating is via a covalent bond.

32. The conjugate of claim 29, wherein said conjugating is via a non-covalent bond.

33. The conjugate of claim 29, wherein said detoxified ETA is produced recombinantly.

34. The conjugate of claim 29, wherein said detoxified ETA contains a sulfur residue not found in the natural toxin.

35. The conjugate of claim 29, wherein said detoxified ETA contains a deletion of the glutamate residue at position 553 of the natural toxin.

36. The conjugate of claim 30, wherein said molecule is a nucleic acid.

37. The conjugate of claim 30, wherein said molecule is a peptide.

38. The conjugate of claim 30, wherein said molecule is a peptide-nucleic acid.

39. The conjugate of claim 30, wherein said molecule is an antibody.

40. The conjugate of claim 30, wherein said molecule is a single chain antibody.

41. The conjugate of claim 30, wherein said molecule is a pharmaceutical.

42. The conjugate of claim 39, wherein said antibody has catalytic function.

43. The conjugate of claim 36, wherein said nucleic acid is DNA.

44. The conjugate of claim 37, wherein said peptide is a polypeptide.

45. The conjugate of claim 40, wherein said single-chain antibody has catalytic function.

46. The conjugate of claim 43, wherein said DNA is under the control of a eukaryotic promoter.

47. The conjugate of claim 46, wherein said DNA encodes a nucleic acid binding protein, a single-chain antibody, a tumor suppressor, a cytokine, an oncogene, a hormone or a toxin.

48. The conjugate of claim 46, wherein said eukaryotic promoter is the CMV IE promoter, the β-actin promoter, the E1A promoter, the TET promoter or the ecdysone promoter.

49. The conjugate of claim 46, wherein said DNA encodes an antisense construct.

50. The conjugate of claim 49, wherein said antisense construct targets an oncogene or a viral protein.

51. The conjugate of claim 44, wherein said polypeptide is an enzyme, an antibody or a nucleic acid binding protein.

52. The conjugate of claim 31, wherein said bond is a carbon-sulfur bond, carbon-carbon bond, carbon-oxygen bond or a carbon-nitrogen bond.

53. The conjugate of claim 52, wherein said bond is a carbon-sulfur bond, and the sulfur residue of said carbon-sulfur bond is a component of said detoxified ETA.

54. A pharmaceutical composition comprising:
(i) an ETA conjugate comprising
   (a) a detoxified ETA, wherein said detoxified ETA contains a deletion, insertion or substitution in domain III of ETA,
   (b) another molecule conjugated to said detoxified ETA in domain III; and
(ii) a pharmaceutically acceptable buffer diluent or excipient.

55. The pharmaceutical composition of claim 54, wherein said molecule is a nucleic acid, a peptide, a peptide-nucleic acid, an antibody, a single-chain antibody or a pharmaceutical.

56. The pharmaceutical composition of claim 55, wherein said molecule is a nucleic acid.

57. The pharmaceutical composition of claim 55, wherein said molecule is a peptide.

58. The pharmaceutical composition of claim 55, wherein said molecule is a peptide-nucleic acid.

59. The pharmaceutical composition of claim 55, wherein said molecule is an antibody.

60. The pharmaceutical composition of claim 55, wherein said molecule is a single chain antibody.

61. The pharmaceutical composition of claim 54, wherein said detoxified ETA contains a deletion of the glutamate residue at position 553 of the natural toxin.

62. The pharmaceutical composition of claim 55, wherein said molecule is a pharmaceutical.

* * * * *